(12) United States Patent
Paré et al.

(10) Patent No.: US 11,065,047 B2
(45) Date of Patent: Jul. 20, 2021

(54) SYSTEMS, APPARATUSES, AND METHODS FOR PROTECTING ELECTRONIC COMPONENTS FROM HIGH POWER NOISE INDUCED BY HIGH VOLTAGE PULSES

(71) Applicant: Farapulse, Inc., Menlo Park, CA (US)

(72) Inventors: Michael Alan Paré, San Carlos, CA (US); Shailendhar Saraf, San Jose, CA (US)

(73) Assignee: Farapulse, Inc., Menlo Park, CA (US)

( * ) Notice: Subject to any disclaimer, the term of this patent is extended or adjusted under 35 U.S.C. 154(b) by 0 days.

(21) Appl. No.: 16/689,967

(22) Filed: Nov. 20, 2019

(65) Prior Publication Data

US 2021/0145503 A1     May 20, 2021

(51) Int. Cl.
*A61B 18/12* (2006.01)
*A61B 18/14* (2006.01)
(Continued)

(52) U.S. Cl.
CPC ...... *A61B 18/1206* (2013.01); *A61B 18/1233* (2013.01); *A61B 18/14* (2013.01);
(Continued)

(58) Field of Classification Search
CPC .............. A61N 1/3718; A61B 18/1233; A61B 2018/124; A61B 2018/1293;
(Continued)

(56) References Cited

U.S. PATENT DOCUMENTS

| | | |
|---|---|---|
| 4,200,104 A | 4/1980 | Harris |
| 4,438,766 A | 3/1984 | Bowers |

(Continued)

FOREIGN PATENT DOCUMENTS

| | | |
|---|---|---|
| CN | 105283143 A | 1/2016 |
| EP | 1042990 A1 | 10/2000 |

(Continued)

OTHER PUBLICATIONS

Partial Supplementary European Search Report for European Application No. 13827672.0, dated Mar. 23, 2016, 6 pages.
(Continued)

*Primary Examiner* — Jaymi E Della
*Assistant Examiner* — Sean W Collins
(74) *Attorney, Agent, or Firm* — Cooley LLP

(57) ABSTRACT

Systems, devices, and methods for electroporation ablation therapy are disclosed, with a protection device for isolating electronic circuitry, devices, and/or other components from a set of electrodes during a cardiac ablation procedure. A system can include a first set of electrodes disposable near cardiac tissue of a heart and a second set of electrodes disposable in contact with patient anatomy. The system can further include a signal generator configured to generate a pulse waveform, where the signal generator coupled to the first set of electrodes and configured to repeatedly deliver the pulse waveform to the first set of electrodes. The system can further include a protection device configured to selectively couple and decouple an electronic device to the second set of electrodes.

25 Claims, 16 Drawing Sheets

(51) Int. Cl.
*A61N 1/37* (2006.01)
*A61B 34/20* (2016.01)
*A61B 5/352* (2021.01)
*A61B 18/00* (2006.01)
*A61N 1/362* (2006.01)
*A61N 1/05* (2006.01)

(52) U.S. Cl.
CPC ........ *A61B 18/1492* (2013.01); *A61N 1/3718* (2013.01); *A61B 5/352* (2021.01); *A61B 34/20* (2016.02); *A61B 2018/00351* (2013.01); *A61B 2018/00357* (2013.01); *A61B 2018/00375* (2013.01); *A61B 2018/00577* (2013.01); *A61B 2018/00613* (2013.01); *A61B 2018/00839* (2013.01); *A61B 2018/1293* (2013.01); *A61N 1/056* (2013.01); *A61N 1/362* (2013.01)

(58) Field of Classification Search
CPC ................ A61B 18/1206; A61B 18/14; A61B 2018/00577; A61B 2018/00351; A61B 5/0456; A61B 2018/00839; A61B 2018/00613; A61B 34/20
See application file for complete search history.

(56) References Cited

U.S. PATENT DOCUMENTS

| | | | |
|---|---|---|---|
| 4,470,407 | A | 9/1984 | Hussein |
| 4,739,759 | A | 4/1988 | Rexroth et al. |
| 5,234,004 | A | 8/1993 | Hascoet et al. |
| 5,242,441 | A | 9/1993 | Avitall |
| 5,257,635 | A | 11/1993 | Langberg |
| 5,281,213 | A | 1/1994 | Milder et al. |
| 5,304,214 | A | 4/1994 | DeFord et al. |
| 5,306,296 | A | 4/1994 | Wright et al. |
| 5,334,193 | A | 8/1994 | Nardella |
| 5,341,807 | A | 8/1994 | Nardella |
| 5,342,301 | A | 8/1994 | Saab |
| 5,398,683 | A | 3/1995 | Edwards et al. |
| 5,443,463 | A | 8/1995 | Stern et al. |
| 5,454,370 | A | 10/1995 | Avitall |
| 5,515,848 | A | 5/1996 | Corbett, III et al. |
| 5,531,685 | A | 7/1996 | Hemmer et al. |
| 5,545,161 | A | 8/1996 | Imran |
| 5,558,091 | A | 9/1996 | Acker et al. |
| 5,578,040 | A | 11/1996 | Smith |
| 5,617,854 | A | 4/1997 | Munsif |
| 5,624,430 | A | 4/1997 | Eton et al. |
| 5,662,108 | A | 9/1997 | Budd et al. |
| 5,667,491 | A | 9/1997 | Pliquett et al. |
| 5,672,170 | A | 9/1997 | Cho |
| 5,700,243 | A | 12/1997 | Narciso, Jr. |
| 5,702,438 | A | 12/1997 | Avitall |
| 5,706,823 | A | 1/1998 | Wodlinger |
| 5,722,400 | A | 3/1998 | Ockuly et al. |
| 5,722,402 | A | 3/1998 | Swanson et al. |
| 5,749,914 | A | 5/1998 | Janssen |
| 5,779,699 | A | 7/1998 | Lipson |
| 5,788,692 | A | 8/1998 | Campbell et al. |
| 5,810,762 | A | 9/1998 | Hofmann |
| 5,833,710 | A | 11/1998 | Jacobson |
| 5,836,874 | A | 11/1998 | Swanson et al. |
| 5,836,942 | A | 11/1998 | Netherly et al. |
| 5,836,947 | A | 11/1998 | Fleischman et al. |
| 5,843,154 | A | 12/1998 | Osypka |
| 5,849,028 | A | 12/1998 | Chen |
| 5,863,291 | A | 1/1999 | Schaer |
| 5,868,736 | A | 2/1999 | Swanson et al. |
| 5,871,523 | A | 2/1999 | Fleischman et al. |
| 5,876,336 | A | 3/1999 | Swanson et al. |
| 5,885,278 | A | 3/1999 | Fleischman et al. |
| 5,895,404 | A | 4/1999 | Ruiz |
| 5,899,917 | A | 5/1999 | Edwards et al. |
| 5,904,709 | A | 5/1999 | Arndt et al. |
| 5,916,158 | A | 6/1999 | Webster, Jr. |
| 5,916,213 | A | 6/1999 | Haissaguerre et al. |
| 5,921,924 | A | 7/1999 | Avitall |
| 5,928,269 | A | 7/1999 | Alt |
| 5,928,270 | A | 7/1999 | Ramsey, III |
| 6,002,955 | A | 12/1999 | Willems et al. |
| 6,006,131 | A | 12/1999 | Cooper et al. |
| 6,009,351 | A | 12/1999 | Flachman |
| 6,014,579 | A | 1/2000 | Pomeranz et al. |
| 6,029,671 | A | 2/2000 | Stevens et al. |
| 6,033,403 | A | 3/2000 | Tu et al. |
| 6,035,238 | A | 3/2000 | Ingle et al. |
| 6,045,550 | A | 4/2000 | Simpson et al. |
| 6,068,653 | A | 5/2000 | LaFontaine |
| 6,071,274 | A | 6/2000 | Thompson et al. |
| 6,071,281 | A | 6/2000 | Burnside et al. |
| 6,074,389 | A | 6/2000 | Levine et al. |
| 6,076,012 | A | 6/2000 | Swanson et al. |
| 6,090,104 | A | 7/2000 | Webster, Jr. |
| 6,096,036 | A | 8/2000 | Bowe et al. |
| 6,113,595 | A | 9/2000 | Muntermann |
| 6,119,041 | A | 9/2000 | Pomeranz et al. |
| 6,120,500 | A | 9/2000 | Bednarek et al. |
| 6,146,381 | A | 11/2000 | Bowe et al. |
| 6,164,283 | A | 12/2000 | Lesh |
| 6,167,291 | A | 12/2000 | Barajas et al. |
| 6,171,305 | B1 | 1/2001 | Sherman |
| 6,216,034 | B1 | 4/2001 | Hofmann et al. |
| 6,219,582 | B1 | 4/2001 | Hofstad et al. |
| 6,223,085 | B1 | 4/2001 | Dann et al. |
| 6,231,518 | B1 | 5/2001 | Grabek et al. |
| 6,245,064 | B1 | 6/2001 | Lesh et al. |
| 6,251,107 | B1 | 6/2001 | Schaer |
| 6,251,128 | B1 | 6/2001 | Knopp et al. |
| 6,270,476 | B1 | 8/2001 | Santoianni et al. |
| 6,272,384 | B1 | 8/2001 | Simon et al. |
| 6,287,306 | B1 | 9/2001 | Kroll et al. |
| 6,314,963 | B1 | 11/2001 | Vaska et al. |
| 6,322,559 | B1 | 11/2001 | Daulton et al. |
| 6,350,263 | B1 | 2/2002 | Wetzig et al. |
| 6,370,412 | B1 | 4/2002 | Armoundas et al. |
| 6,391,024 | B1 | 5/2002 | Sun et al. |
| 6,447,505 | B2 | 9/2002 | McGovern et al. |
| 6,464,699 | B1 | 10/2002 | Swanson |
| 6,470,211 | B1 | 10/2002 | Ideker et al. |
| 6,502,576 | B1 | 1/2003 | Lesh |
| 6,503,247 | B2 | 1/2003 | Swartz et al. |
| 6,517,534 | B1 | 2/2003 | McGovern et al. |
| 6,527,724 | B1 | 3/2003 | Fenici |
| 6,527,767 | B2 | 3/2003 | Wang et al. |
| 6,592,581 | B2 | 7/2003 | Bowe |
| 6,595,991 | B2 | 7/2003 | Tollner et al. |
| 6,607,520 | B2 | 8/2003 | Keane |
| 6,623,480 | B1 | 9/2003 | Kuo et al. |
| 6,638,278 | B2 | 10/2003 | Falwell et al. |
| 6,666,863 | B2 | 12/2003 | Wentzel et al. |
| 6,669,693 | B2 | 12/2003 | Friedman |
| 6,702,811 | B2 | 3/2004 | Stewart et al. |
| 6,719,756 | B1 | 4/2004 | Muntermann |
| 6,723,092 | B2 | 4/2004 | Brown et al. |
| 6,728,563 | B2 | 4/2004 | Rashidi |
| 6,743,225 | B2 | 6/2004 | Sanchez et al. |
| 6,743,226 | B2 | 6/2004 | Cosman et al. |
| 6,743,239 | B1 | 6/2004 | Kuehn et al. |
| 6,764,486 | B2 | 7/2004 | Natale |
| 6,780,181 | B2 | 8/2004 | Kroll et al. |
| 6,805,128 | B1 | 10/2004 | Pless |
| 6,807,447 | B2 | 10/2004 | Griffin, III |
| 6,892,091 | B1 | 5/2005 | Ben-Haim et al. |
| 6,893,438 | B2 | 5/2005 | Hall et al. |
| 6,926,714 | B1 | 8/2005 | Sra |
| 6,955,173 | B2 | 10/2005 | Lesh |
| 6,960,206 | B2 | 11/2005 | Keane |
| 6,960,207 | B2 | 11/2005 | Vanney et al. |
| 6,972,016 | B2 | 12/2005 | Hill, III et al. |
| 6,973,339 | B2 | 12/2005 | Govari |
| 6,979,331 | B2 | 12/2005 | Hintringer et al. |
| 6,984,232 | B2 | 1/2006 | Vanney et al. |
| 6,985,776 | B2 | 1/2006 | Kane et al. |

(56) References Cited

U.S. PATENT DOCUMENTS

| | | |
|---|---|---|
| 7,001,383 B2 | 2/2006 | Keidar |
| 7,041,095 B2 | 5/2006 | Wang et al. |
| 7,113,831 B2 | 9/2006 | Hooven |
| 7,171,263 B2 | 1/2007 | Darvish et al. |
| 7,182,725 B2 | 2/2007 | Bonan et al. |
| 7,195,628 B2 | 3/2007 | Falkenberg |
| 7,207,988 B2 | 4/2007 | Leckrone et al. |
| 7,207,989 B2 | 4/2007 | Pike, Jr. et al. |
| 7,229,402 B2 | 6/2007 | Diaz et al. |
| 7,229,437 B2 | 6/2007 | Johnson et al. |
| 7,250,049 B2 | 7/2007 | Roop et al. |
| 7,285,116 B2 | 10/2007 | de la Rama et al. |
| 7,285,119 B2 | 10/2007 | Stewart et al. |
| 7,326,208 B2 | 2/2008 | Vanney et al. |
| 7,346,379 B2 | 3/2008 | Eng et al. |
| 7,367,974 B2 | 5/2008 | Haemmerich et al. |
| 7,374,567 B2 | 5/2008 | Heuser |
| 7,387,629 B2 | 6/2008 | Vanney et al. |
| 7,387,630 B2 | 6/2008 | Mest |
| 7,387,636 B2 | 6/2008 | Cohn et al. |
| 7,416,552 B2 | 8/2008 | Paul et al. |
| 7,419,477 B2 | 9/2008 | Simpson et al. |
| 7,419,489 B2 | 9/2008 | Vanney et al. |
| 7,422,591 B2 | 9/2008 | Phan |
| 7,429,261 B2 | 9/2008 | Kunis et al. |
| 7,435,248 B2 | 10/2008 | Taimisto et al. |
| 7,513,896 B2 | 4/2009 | Orszulak |
| 7,527,625 B2 | 5/2009 | Knight et al. |
| 7,578,816 B2 | 8/2009 | Boveja et al. |
| 7,588,567 B2 | 9/2009 | Boveja et al. |
| 7,623,899 B2 | 11/2009 | Worley et al. |
| 7,678,108 B2 | 3/2010 | Chrisitian et al. |
| 7,681,579 B2 | 3/2010 | Schwartz |
| 7,771,421 B2 | 8/2010 | Stewart et al. |
| 7,805,182 B2 | 9/2010 | Weese et al. |
| 7,850,642 B2 | 12/2010 | Moll et al. |
| 7,850,685 B2 | 12/2010 | Kunis et al. |
| 7,857,808 B2 | 12/2010 | Oral et al. |
| 7,857,809 B2 | 12/2010 | Drysen |
| 7,869,865 B2 | 1/2011 | Govari et al. |
| 7,896,873 B2 | 3/2011 | Hiller et al. |
| 7,917,211 B2 | 3/2011 | Zacouto |
| 7,918,819 B2 | 4/2011 | Karmarkar et al. |
| 7,918,850 B2 | 4/2011 | Govari et al. |
| 7,922,714 B2 | 4/2011 | Stevens-Wright |
| 7,955,827 B2 | 6/2011 | Rubinsky et al. |
| 8,048,067 B2 | 11/2011 | Davalos et al. |
| 8,048,072 B2 | 11/2011 | Verin et al. |
| 8,100,895 B2 | 1/2012 | Panos et al. |
| 8,100,900 B2 | 1/2012 | Prinz et al. |
| 8,108,069 B2 | 1/2012 | Stahler et al. |
| 8,133,220 B2 | 3/2012 | Lee et al. |
| 8,137,342 B2 | 3/2012 | Crossman |
| 8,145,289 B2 | 3/2012 | Calabro' et al. |
| 8,147,486 B2 | 4/2012 | Honour et al. |
| 8,160,690 B2 | 4/2012 | Wilfley et al. |
| 8,175,680 B2 | 5/2012 | Panescu |
| 8,182,477 B2 | 5/2012 | Orszulak et al. |
| 8,206,384 B2 | 6/2012 | Falwell et al. |
| 8,206,385 B2 | 6/2012 | Stangenes et al. |
| 8,216,221 B2 | 7/2012 | Ibrahim et al. |
| 8,221,411 B2 | 7/2012 | Francischelli et al. |
| 8,226,648 B2 | 7/2012 | Paul et al. |
| 8,228,065 B2 | 7/2012 | Wirtz et al. |
| 8,235,986 B2 | 8/2012 | Kulesa et al. |
| 8,235,988 B2 | 8/2012 | Davis et al. |
| 8,251,986 B2 | 8/2012 | Chornenky et al. |
| 8,282,631 B2 | 10/2012 | Davalos et al. |
| 8,287,532 B2 | 10/2012 | Carroll et al. |
| 8,414,508 B2 | 4/2013 | Thapliyal et al. |
| 8,430,875 B2 | 4/2013 | Ibrahim et al. |
| 8,433,394 B2 | 4/2013 | Harlev et al. |
| 8,449,535 B2 | 5/2013 | Deno et al. |
| 8,454,594 B2 | 6/2013 | Demarais et al. |
| 8,463,368 B2 | 6/2013 | Harlev et al. |
| 8,475,450 B2 | 7/2013 | Govari et al. |
| 8,486,063 B2 | 7/2013 | Werneth et al. |
| 8,500,733 B2 | 8/2013 | Watson |
| 8,535,304 B2 | 9/2013 | Sklar et al. |
| 8,538,501 B2 | 9/2013 | Venkatachalam et al. |
| 8,562,588 B2 | 10/2013 | Hobbs et al. |
| 8,568,406 B2 | 10/2013 | Harlev et al. |
| 8,571,635 B2 | 10/2013 | McGee |
| 8,571,647 B2 | 10/2013 | Harlev et al. |
| 8,585,695 B2 | 11/2013 | Shih |
| 8,588,885 B2 | 11/2013 | Hall et al. |
| 8,597,288 B2 | 12/2013 | Christian |
| 8,608,735 B2 | 12/2013 | Govari et al. |
| 8,628,522 B2 | 1/2014 | Ibrahim et al. |
| 8,632,534 B2 | 1/2014 | Pearson et al. |
| 8,647,338 B2 | 2/2014 | Chornenky et al. |
| 8,708,952 B2 | 4/2014 | Cohen et al. |
| 8,734,442 B2 | 5/2014 | Cao et al. |
| 8,771,267 B2 | 7/2014 | Kunis et al. |
| 8,795,310 B2 | 8/2014 | Fung et al. |
| 8,808,273 B2 | 8/2014 | Caples et al. |
| 8,808,281 B2 | 8/2014 | Emons et al. |
| 8,834,461 B2 | 9/2014 | Werneth et al. |
| 8,834,464 B2 | 9/2014 | Stewart et al. |
| 8,868,169 B2 | 10/2014 | Narayan et al. |
| 8,876,817 B2 | 11/2014 | Avitall et al. |
| 8,880,195 B2 | 11/2014 | Azure |
| 8,886,309 B2 | 11/2014 | Luther et al. |
| 8,903,488 B2 | 12/2014 | Callas et al. |
| 8,920,411 B2 | 12/2014 | Gelbart et al. |
| 8,926,589 B2 | 1/2015 | Govari |
| 8,932,287 B2 | 1/2015 | Gelbart et al. |
| 8,945,117 B2 | 2/2015 | Bencini |
| 8,979,841 B2 | 3/2015 | Kunis et al. |
| 8,986,278 B2 | 3/2015 | Fung et al. |
| 9,002,442 B2 | 4/2015 | Harley et al. |
| 9,005,189 B2 | 4/2015 | Davalos et al. |
| 9,005,194 B2 | 4/2015 | Oral et al. |
| 9,011,425 B2 | 4/2015 | Fischer et al. |
| 9,044,245 B2 | 6/2015 | Condie et al. |
| 9,055,959 B2 | 6/2015 | Vaska et al. |
| 9,072,518 B2 | 7/2015 | Swanson |
| 9,078,667 B2 | 7/2015 | Besser et al. |
| 9,101,374 B1 | 8/2015 | Hoch et al. |
| 9,119,533 B2 | 9/2015 | Ghaffari |
| 9,119,634 B2 | 9/2015 | Gelbart et al. |
| 9,131,897 B2 | 9/2015 | Harada et al. |
| 9,155,590 B2 | 10/2015 | Mathur |
| 9,162,037 B2 | 10/2015 | Belson et al. |
| 9,179,972 B2 | 11/2015 | Olson |
| 9,186,481 B2 | 11/2015 | Avitall et al. |
| 9,192,769 B2 | 11/2015 | Donofrio et al. |
| 9,211,405 B2 | 12/2015 | Mahapatra et al. |
| 9,216,055 B2 | 12/2015 | Spence et al. |
| 9,233,248 B2 | 1/2016 | Luther et al. |
| 9,237,926 B2 | 1/2016 | Nollert et al. |
| 9,262,252 B2 | 2/2016 | Kirkpatrick et al. |
| 9,277,957 B2 | 3/2016 | Long et al. |
| 9,282,910 B2 | 3/2016 | Narayan et al. |
| 9,289,258 B2 | 3/2016 | Cohen |
| 9,289,606 B2 | 3/2016 | Paul et al. |
| 9,295,516 B2 | 3/2016 | Pearson et al. |
| 9,301,801 B2 | 4/2016 | Scheib |
| 9,375,268 B2 | 6/2016 | Long |
| 9,414,881 B2 | 8/2016 | Callas et al. |
| 9,468,495 B2 | 10/2016 | Kunis et al. |
| 9,474,486 B2 | 10/2016 | Eliason et al. |
| 9,474,574 B2 | 10/2016 | Ibrahim et al. |
| 9,480,525 B2 | 11/2016 | Lopes et al. |
| 9,486,272 B2 | 11/2016 | Bonyak et al. |
| 9,486,273 B2 | 11/2016 | Lopes et al. |
| 9,492,227 B2 | 11/2016 | Lopes et al. |
| 9,492,228 B2 | 11/2016 | Lopes et al. |
| 9,517,103 B2 | 12/2016 | Panescu et al. |
| 9,526,573 B2 | 12/2016 | Lopes et al. |
| 9,532,831 B2 | 1/2017 | Reinders et al. |
| 9,539,010 B2 | 1/2017 | Gagner et al. |
| 9,554,848 B2 | 1/2017 | Stewart et al. |
| 9,554,851 B2 | 1/2017 | Sklar et al. |

(56) References Cited

U.S. PATENT DOCUMENTS

| | | |
|---|---|---|
| 9,700,368 B2 | 7/2017 | Callas et al. |
| 9,724,170 B2 | 8/2017 | Mickelsen |
| 9,757,193 B2 | 9/2017 | Zarins et al. |
| 9,782,099 B2 | 10/2017 | Williams et al. |
| 9,788,885 B2 | 10/2017 | Long et al. |
| 9,795,442 B2 | 10/2017 | Salahieh et al. |
| 9,861,802 B2 | 1/2018 | Mickelsen |
| 9,913,685 B2 | 3/2018 | Clark et al. |
| 9,931,487 B2 | 4/2018 | Quinn et al. |
| 9,987,081 B1 | 6/2018 | Bowers et al. |
| 9,999,465 B2 | 6/2018 | Long et al. |
| 10,016,232 B1 | 7/2018 | Bowers et al. |
| 10,117,701 B2 | 11/2018 | Davalos et al. |
| 10,117,707 B2 | 11/2018 | Garcia et al. |
| 10,130,423 B1 | 11/2018 | Viswanathan et al. |
| 10,172,673 B2 | 1/2019 | Viswanathan et al. |
| 10,292,755 B2 | 5/2019 | Arena et al. |
| 10,322,286 B2 | 6/2019 | Viswanathan et al. |
| 10,342,598 B2 | 7/2019 | Long et al. |
| 10,433,906 B2 | 10/2019 | Mickelsen |
| 10,433,908 B2 | 10/2019 | Viswanathan et al. |
| 10,448,989 B2 | 10/2019 | Arena et al. |
| 10,507,302 B2 | 12/2019 | Leeflang et al. |
| 10,512,505 B2 | 12/2019 | Viswanathan |
| 10,512,779 B2 | 12/2019 | Viswanathan et al. |
| 10,517,672 B2 | 12/2019 | Long |
| 10,531,914 B2 | 1/2020 | Stewart et al. |
| 10,625,080 B1 | 4/2020 | Viswanathan |
| 10,688,305 B1 | 6/2020 | Viswanathan |
| 10,709,502 B2 | 7/2020 | Viswanathan |
| 10,709,891 B2 | 7/2020 | Viswanathan et al. |
| 2001/0000791 A1 | 5/2001 | Suorsa et al. |
| 2001/0007070 A1 | 7/2001 | Stewart et al. |
| 2001/0044624 A1 | 11/2001 | Seraj et al. |
| 2002/0052602 A1 | 5/2002 | Wang et al. |
| 2002/0077627 A1 | 6/2002 | Johnson et al. |
| 2002/0087169 A1 | 7/2002 | Brock et al. |
| 2002/0091384 A1 | 7/2002 | Hooven et al. |
| 2002/0095176 A1 | 7/2002 | Liddicoat et al. |
| 2002/0111618 A1 | 8/2002 | Stewart et al. |
| 2002/0156526 A1 | 10/2002 | Hlavka et al. |
| 2002/0161323 A1 | 10/2002 | Miller et al. |
| 2002/0169445 A1 | 11/2002 | Jain et al. |
| 2002/0177765 A1 | 11/2002 | Bowe et al. |
| 2002/0183638 A1 | 12/2002 | Swanson |
| 2003/0014098 A1 | 1/2003 | Quijano et al. |
| 2003/0018374 A1 | 1/2003 | Paulos |
| 2003/0023287 A1 | 1/2003 | Edwards et al. |
| 2003/0028189 A1 | 2/2003 | Woloszko et al. |
| 2003/0050637 A1 | 3/2003 | Maguire et al. |
| 2003/0078494 A1 | 4/2003 | Panescu et al. |
| 2003/0114849 A1 | 6/2003 | Ryan |
| 2003/0125729 A1 | 7/2003 | Hooven et al. |
| 2003/0130598 A1 | 7/2003 | Manning et al. |
| 2003/0130711 A1 | 7/2003 | Pearson et al. |
| 2003/0204161 A1 | 10/2003 | Ferek Petric |
| 2003/0229379 A1 | 12/2003 | Ramsey |
| 2004/0039382 A1 | 2/2004 | Kroll et al. |
| 2004/0049181 A1 | 3/2004 | Stewart et al. |
| 2004/0049182 A1 | 3/2004 | Koblish et al. |
| 2004/0082859 A1 | 4/2004 | Schaer |
| 2004/0082948 A1 | 4/2004 | Stewart et al. |
| 2004/0087939 A1 | 5/2004 | Eggers et al. |
| 2004/0111087 A1 | 6/2004 | Stern et al. |
| 2004/0147920 A1 | 7/2004 | Keidar |
| 2004/0199157 A1 | 10/2004 | Palanker et al. |
| 2004/0215139 A1 | 10/2004 | Cohen |
| 2004/0231683 A1 | 11/2004 | Eng et al. |
| 2004/0236360 A1 | 11/2004 | Cohn et al. |
| 2004/0254607 A1 | 12/2004 | Wittenberger et al. |
| 2004/0267337 A1 | 12/2004 | Hayzelden |
| 2005/0033282 A1 | 2/2005 | Hooven |
| 2005/0187545 A1 | 8/2005 | Hooven et al. |
| 2005/0222632 A1 | 10/2005 | Obino |
| 2005/0251130 A1 | 11/2005 | Boveja et al. |
| 2005/0261672 A1 | 11/2005 | Deem et al. |
| 2006/0009755 A1 | 1/2006 | Sra |
| 2006/0009759 A1 | 1/2006 | Chrisitian et al. |
| 2006/0015095 A1 | 1/2006 | Desinger et al. |
| 2006/0015165 A1 | 1/2006 | Bertolero et al. |
| 2006/0024359 A1 | 2/2006 | Walker et al. |
| 2006/0058781 A1 | 3/2006 | Long |
| 2006/0111702 A1 | 5/2006 | Oral et al. |
| 2006/0142801 A1 | 6/2006 | Demarais et al. |
| 2006/0167448 A1 | 7/2006 | Kozel |
| 2006/0217703 A1 | 9/2006 | Chornenky et al. |
| 2006/0241734 A1 | 10/2006 | Marshall et al. |
| 2006/0264752 A1 | 11/2006 | Rubinsky et al. |
| 2006/0270900 A1 | 11/2006 | Chin et al. |
| 2006/0287648 A1 | 12/2006 | Schwartz |
| 2006/0293730 A1 | 12/2006 | Rubinsky et al. |
| 2006/0293731 A1 | 12/2006 | Rubinsky et al. |
| 2007/0005053 A1 | 1/2007 | Dando |
| 2007/0021744 A1 | 1/2007 | Creighton |
| 2007/0060989 A1 | 3/2007 | Deem et al. |
| 2007/0066972 A1 | 3/2007 | Ormsby et al. |
| 2007/0129721 A1 | 6/2007 | Phan et al. |
| 2007/0129760 A1 | 6/2007 | Demarais et al. |
| 2007/0156135 A1 | 7/2007 | Rubinsky et al. |
| 2007/0167740 A1 | 7/2007 | Grunewald et al. |
| 2007/0167940 A1 | 7/2007 | Stevens-Wright |
| 2007/0173878 A1 | 7/2007 | Heuser |
| 2007/0208329 A1 | 9/2007 | Ward et al. |
| 2007/0225589 A1 | 9/2007 | Viswanathan |
| 2007/0249923 A1 | 10/2007 | Keenan |
| 2007/0260223 A1 | 11/2007 | Scheibe et al. |
| 2007/0270792 A1 | 11/2007 | Hennemann et al. |
| 2008/0009855 A1 | 1/2008 | Hamou |
| 2008/0033426 A1 | 2/2008 | Machell |
| 2008/0065061 A1 | 3/2008 | Viswanathan |
| 2008/0086120 A1 | 4/2008 | Mirza et al. |
| 2008/0091195 A1 | 4/2008 | Silwa et al. |
| 2008/0103545 A1 | 5/2008 | Bolea et al. |
| 2008/0132885 A1 | 6/2008 | Rubinsky et al. |
| 2008/0161789 A1 | 7/2008 | Thao et al. |
| 2008/0172048 A1 | 7/2008 | Martin et al. |
| 2008/0200913 A1 | 8/2008 | Viswanathan |
| 2008/0208118 A1 | 8/2008 | Goldman |
| 2008/0243214 A1 | 10/2008 | Koblish |
| 2008/0281322 A1 | 11/2008 | Sherman et al. |
| 2008/0300574 A1 | 12/2008 | Belson et al. |
| 2008/0300588 A1 | 12/2008 | Groth et al. |
| 2009/0024084 A1 | 1/2009 | Khosla et al. |
| 2009/0048591 A1 | 2/2009 | Ibrahim et al. |
| 2009/0062788 A1 | 3/2009 | Long et al. |
| 2009/0076500 A1 | 3/2009 | Azure |
| 2009/0105654 A1 | 4/2009 | Kurth et al. |
| 2009/0138009 A1 | 5/2009 | Viswanathan et al. |
| 2009/0149917 A1 | 6/2009 | Whitehurst et al. |
| 2009/0163905 A1 | 6/2009 | Winkler et al. |
| 2009/0228003 A1 | 9/2009 | Sinelnikov |
| 2009/0240248 A1 | 9/2009 | Deford et al. |
| 2009/0275827 A1 | 11/2009 | Aiken et al. |
| 2009/0281477 A1 | 11/2009 | Mikus et al. |
| 2009/0306651 A1 | 12/2009 | Schneider |
| 2010/0004623 A1 | 1/2010 | Hamilton et al. |
| 2010/0023004 A1 | 1/2010 | Francischelli et al. |
| 2010/0134273 A1* | 6/2010 | Weiss ............... G01R 33/285 340/532 |
| 2010/0135550 A1 | 6/2010 | Arnon |
| 2010/0137861 A1 | 6/2010 | Soroff et al. |
| 2010/0168550 A1 | 7/2010 | Byrd et al. |
| 2010/0185140 A1 | 7/2010 | Kassab et al. |
| 2010/0185186 A1 | 7/2010 | Longoria |
| 2010/0191112 A1 | 7/2010 | Demarais et al. |
| 2010/0191232 A1 | 7/2010 | Boveda |
| 2010/0241185 A1 | 9/2010 | Mahapatra et al. |
| 2010/0261994 A1 | 10/2010 | Davalos et al. |
| 2010/0274238 A1 | 10/2010 | Klimovitch |
| 2010/0280513 A1 | 11/2010 | Juergen et al. |
| 2010/0280539 A1 | 11/2010 | Miyoshi et al. |
| 2010/0292687 A1 | 11/2010 | Kauphusman et al. |
| 2010/0312096 A1 | 12/2010 | Guttman et al. |
| 2010/0312300 A1 | 12/2010 | Ryu et al. |

(56) References Cited

U.S. PATENT DOCUMENTS

| | | |
|---|---|---|
| 2011/0015628 A1 | 1/2011 | Dalal et al. |
| 2011/0028962 A1 | 2/2011 | Werneth et al. |
| 2011/0028964 A1 | 2/2011 | Edwards |
| 2011/0040199 A1 | 2/2011 | Hopenfeld |
| 2011/0098694 A1 | 4/2011 | Long |
| 2011/0106221 A1 | 5/2011 | Neal, II et al. |
| 2011/0130708 A1 | 6/2011 | Perry et al. |
| 2011/0144524 A1 | 6/2011 | Fish et al. |
| 2011/0144633 A1 | 6/2011 | Govari |
| 2011/0160785 A1 | 6/2011 | Mori et al. |
| 2011/0190659 A1 | 8/2011 | Long et al. |
| 2011/0190727 A1 | 8/2011 | Edmunds et al. |
| 2011/0213231 A1 | 9/2011 | Hall et al. |
| 2011/0276047 A1 | 11/2011 | Sklar et al. |
| 2011/0276075 A1 | 11/2011 | Fung et al. |
| 2011/0288544 A1 | 11/2011 | Verin et al. |
| 2011/0288547 A1 | 11/2011 | Morgan et al. |
| 2011/0313417 A1 | 12/2011 | De La Rama et al. |
| 2012/0029512 A1 | 2/2012 | Willard et al. |
| 2012/0046570 A1 | 2/2012 | Villegas et al. |
| 2012/0053581 A1 | 3/2012 | Wittkampf et al. |
| 2012/0059255 A1 | 3/2012 | Paul et al. |
| 2012/0071872 A1 | 3/2012 | Rubinsky et al. |
| 2012/0078320 A1 | 3/2012 | Schotzko et al. |
| 2012/0078343 A1 | 3/2012 | Fish |
| 2012/0089089 A1 | 4/2012 | Swain et al. |
| 2012/0095459 A1 | 4/2012 | Callas et al. |
| 2012/0101413 A1 | 4/2012 | Beetel et al. |
| 2012/0109242 A1* | 5/2012 | Levin .................. A61B 5/04288 607/17 |
| 2012/0158021 A1 | 6/2012 | Morrill |
| 2012/0165667 A1 | 6/2012 | Altmann et al. |
| 2012/0172859 A1 | 7/2012 | Condie et al. |
| 2012/0172867 A1* | 7/2012 | Ryu .................. A61B 18/1492 606/41 |
| 2012/0197100 A1 | 8/2012 | Razavi et al. |
| 2012/0209260 A1 | 8/2012 | Lambert et al. |
| 2012/0220998 A1 | 8/2012 | Long et al. |
| 2012/0265198 A1 | 10/2012 | Crow et al. |
| 2012/0283582 A1 | 11/2012 | Mahapatra et al. |
| 2012/0303019 A1 | 11/2012 | Zhao et al. |
| 2012/0310052 A1 | 12/2012 | Mahapatra et al. |
| 2012/0310230 A1 | 12/2012 | Willis |
| 2012/0310237 A1 | 12/2012 | Swanson |
| 2012/0316557 A1 | 12/2012 | Sartor et al. |
| 2013/0030430 A1 | 1/2013 | Stewart et al. |
| 2013/0060247 A1 | 3/2013 | Sklar et al. |
| 2013/0060248 A1 | 3/2013 | Sklar et al. |
| 2013/0079768 A1 | 3/2013 | De Luca et al. |
| 2013/0090651 A1 | 4/2013 | Smith |
| 2013/0096655 A1 | 4/2013 | Moffitt et al. |
| 2013/0103027 A1 | 4/2013 | Sklar et al. |
| 2013/0103064 A1 | 4/2013 | Arenson et al. |
| 2013/0131662 A1* | 5/2013 | Wittkampf ......... A61B 18/1206 606/34 |
| 2013/0158538 A1 | 6/2013 | Govari |
| 2013/0158621 A1 | 6/2013 | Ding et al. |
| 2013/0172715 A1 | 7/2013 | Just et al. |
| 2013/0172864 A1 | 7/2013 | Ibrahim et al. |
| 2013/0172875 A1 | 7/2013 | Govari et al. |
| 2013/0184702 A1 | 7/2013 | Neal, II et al. |
| 2013/0218157 A1 | 8/2013 | Callas et al. |
| 2013/0226174 A1 | 8/2013 | Ibrahim et al. |
| 2013/0237984 A1 | 9/2013 | Sklar |
| 2013/0253415 A1 | 9/2013 | Sano et al. |
| 2013/0296679 A1 | 11/2013 | Condie et al. |
| 2013/0310829 A1 | 11/2013 | Cohen |
| 2013/0317385 A1 | 11/2013 | Sklar et al. |
| 2013/0331831 A1 | 12/2013 | Werneth et al. |
| 2013/0338467 A1 | 12/2013 | Grasse et al. |
| 2014/0005664 A1 | 1/2014 | Govari et al. |
| 2014/0024911 A1 | 1/2014 | Harlev et al. |
| 2014/0039288 A1 | 2/2014 | Shih |
| 2014/0051993 A1 | 2/2014 | McGee |
| 2014/0052118 A1 | 2/2014 | Laske et al. |
| 2014/0052126 A1 | 2/2014 | Long et al. |
| 2014/0052216 A1 | 2/2014 | Long et al. |
| 2014/0058377 A1 | 2/2014 | Deem et al. |
| 2014/0081113 A1 | 3/2014 | Cohen et al. |
| 2014/0100563 A1 | 4/2014 | Govari et al. |
| 2014/0107644 A1 | 4/2014 | Falwell et al. |
| 2014/0142408 A1 | 5/2014 | De La Rama et al. |
| 2014/0148804 A1 | 5/2014 | Ward et al. |
| 2014/0163480 A1 | 6/2014 | Govari et al. |
| 2014/0163546 A1 | 6/2014 | Govari et al. |
| 2014/0171942 A1 | 6/2014 | Werneth et al. |
| 2014/0180035 A1 | 6/2014 | Anderson |
| 2014/0187916 A1 | 7/2014 | Clark et al. |
| 2014/0194716 A1 | 7/2014 | Diep et al. |
| 2014/0194867 A1 | 7/2014 | Fish et al. |
| 2014/0200567 A1 | 7/2014 | Cox et al. |
| 2014/0235986 A1 | 8/2014 | Harlev et al. |
| 2014/0235988 A1 | 8/2014 | Ghosh |
| 2014/0235989 A1 | 8/2014 | Wodlinger et al. |
| 2014/0243851 A1 | 8/2014 | Cohen et al. |
| 2014/0276760 A1 | 9/2014 | Bonyak et al. |
| 2014/0276782 A1 | 9/2014 | Paskar |
| 2014/0276791 A1 | 9/2014 | Ku et al. |
| 2014/0288556 A1 | 9/2014 | Ibrahim et al. |
| 2014/0303721 A1 | 10/2014 | Fung et al. |
| 2014/0343549 A1 | 11/2014 | Spear et al. |
| 2014/0364845 A1 | 12/2014 | Rashidi |
| 2014/0371613 A1 | 12/2014 | Narayan et al. |
| 2015/0005767 A1 | 1/2015 | Werneth et al. |
| 2015/0011995 A1 | 1/2015 | Avitall et al. |
| 2015/0066108 A1 | 3/2015 | Shi et al. |
| 2015/0080693 A1 | 3/2015 | Solis |
| 2015/0119674 A1 | 4/2015 | Fischell et al. |
| 2015/0126840 A1 | 5/2015 | Thakur et al. |
| 2015/0133914 A1 | 5/2015 | Koblish |
| 2015/0138977 A1 | 5/2015 | Dacosta |
| 2015/0141978 A1 | 5/2015 | Subramaniam et al. |
| 2015/0142041 A1 | 5/2015 | Kendale et al. |
| 2015/0148796 A1 | 5/2015 | Bencini |
| 2015/0150472 A1 | 6/2015 | Harlev et al. |
| 2015/0157402 A1 | 6/2015 | Kunis et al. |
| 2015/0157412 A1 | 6/2015 | Wallace et al. |
| 2015/0164584 A1 | 6/2015 | Davalos et al. |
| 2015/0173824 A1 | 6/2015 | Davalos et al. |
| 2015/0173828 A1 | 6/2015 | Avitall |
| 2015/0174404 A1 | 6/2015 | Rousso et al. |
| 2015/0182740 A1 | 7/2015 | Mickelsen |
| 2015/0196217 A1 | 7/2015 | Harlev et al. |
| 2015/0223726 A1 | 8/2015 | Harlev et al. |
| 2015/0223902 A1 | 8/2015 | Walker et al. |
| 2015/0230699 A1 | 8/2015 | Berul et al. |
| 2015/0258344 A1 | 9/2015 | Tandri et al. |
| 2015/0265342 A1 | 9/2015 | Long et al. |
| 2015/0265344 A1 | 9/2015 | Aktas et al. |
| 2015/0272656 A1 | 10/2015 | Chen |
| 2015/0272664 A9 | 10/2015 | Cohen |
| 2015/0272667 A1 | 10/2015 | Govari et al. |
| 2015/0282729 A1 | 10/2015 | Harlev et al. |
| 2015/0289923 A1 | 10/2015 | Davalos et al. |
| 2015/0304879 A1 | 10/2015 | Dacosta |
| 2015/0320481 A1 | 11/2015 | Cosman et al. |
| 2015/0321021 A1 | 11/2015 | Tandri et al. |
| 2015/0327944 A1 | 11/2015 | Neal, II et al. |
| 2015/0342532 A1 | 12/2015 | Basu et al. |
| 2015/0343212 A1 | 12/2015 | Rousso et al. |
| 2015/0351836 A1 | 12/2015 | Prutchi |
| 2015/0359583 A1 | 12/2015 | Swanson |
| 2016/0000500 A1 | 1/2016 | Salahieh et al. |
| 2016/0008061 A1 | 1/2016 | Fung et al. |
| 2016/0008065 A1 | 1/2016 | Gliner et al. |
| 2016/0029960 A1 | 2/2016 | Toth et al. |
| 2016/0038772 A1 | 2/2016 | Thapliyal et al. |
| 2016/0051204 A1 | 2/2016 | Harlev et al. |
| 2016/0051324 A1 | 2/2016 | Stewart et al. |
| 2016/0058493 A1 | 3/2016 | Neal, II et al. |
| 2016/0058506 A1 | 3/2016 | Spence et al. |
| 2016/0066993 A1 | 3/2016 | Avitall et al. |
| 2016/0074679 A1 | 3/2016 | Thapliyal et al. |
| 2016/0095531 A1 | 4/2016 | Narayan et al. |

(56) References Cited

U.S. PATENT DOCUMENTS

| | | |
|---|---|---|
| 2016/0095642 A1 | 4/2016 | Deno et al. |
| 2016/0095653 A1 | 4/2016 | Lambert et al. |
| 2016/0100797 A1* | 4/2016 | Mahapatra ............... A61B 5/03 600/301 |
| 2016/0100884 A1 | 4/2016 | Fay et al. |
| 2016/0106498 A1 | 4/2016 | Highsmith et al. |
| 2016/0106500 A1 | 4/2016 | Olson |
| 2016/0113709 A1 | 4/2016 | Maor |
| 2016/0113712 A1 | 4/2016 | Cheung et al. |
| 2016/0120564 A1 | 5/2016 | Kirkpatrick et al. |
| 2016/0128770 A1 | 5/2016 | Afonso et al. |
| 2016/0166167 A1 | 6/2016 | Narayan et al. |
| 2016/0166310 A1 | 6/2016 | Stewart et al. |
| 2016/0166311 A1 | 6/2016 | Long et al. |
| 2016/0174865 A1 | 6/2016 | Stewart et al. |
| 2016/0183877 A1 | 6/2016 | Williams et al. |
| 2016/0184003 A1 | 6/2016 | Srimathveeravalli et al. |
| 2016/0184004 A1 | 6/2016 | Hull et al. |
| 2016/0213282 A1 | 7/2016 | Leo et al. |
| 2016/0220307 A1 | 8/2016 | Miller et al. |
| 2016/0235470 A1 | 8/2016 | Callas et al. |
| 2016/0287314 A1 | 10/2016 | Arena et al. |
| 2016/0310211 A1 | 10/2016 | Long |
| 2016/0324564 A1 | 11/2016 | Gerlach et al. |
| 2016/0324573 A1 | 11/2016 | Mickelsen et al. |
| 2016/0331441 A1 | 11/2016 | Konings |
| 2016/0331459 A1 | 11/2016 | Townley et al. |
| 2016/0354142 A1 | 12/2016 | Pearson et al. |
| 2016/0361109 A1 | 12/2016 | Weaver et al. |
| 2017/0001016 A1 | 1/2017 | De Ridder |
| 2017/0035499 A1 | 2/2017 | Stewart et al. |
| 2017/0042449 A1 | 2/2017 | Deno et al. |
| 2017/0042615 A1 | 2/2017 | Salahieh et al. |
| 2017/0056648 A1 | 3/2017 | Syed et al. |
| 2017/0065330 A1 | 3/2017 | Mickelsen et al. |
| 2017/0065339 A1 | 3/2017 | Mickelsen |
| 2017/0065340 A1 | 3/2017 | Long |
| 2017/0065343 A1 | 3/2017 | Mickelsen |
| 2017/0071543 A1 | 3/2017 | Basu et al. |
| 2017/0095291 A1 | 4/2017 | Harrington et al. |
| 2017/0105793 A1 | 4/2017 | Cao et al. |
| 2017/0146584 A1 | 5/2017 | Daw et al. |
| 2017/0151029 A1 | 6/2017 | Mickelsen |
| 2017/0172654 A1 | 6/2017 | Wittkampf et al. |
| 2017/0181795 A1 | 6/2017 | Debruyne |
| 2017/0189097 A1 | 7/2017 | Viswanathan et al. |
| 2017/0215953 A1 | 8/2017 | Long et al. |
| 2017/0245928 A1 | 8/2017 | Xiao et al. |
| 2017/0246455 A1 | 8/2017 | Athos et al. |
| 2017/0312024 A1 | 11/2017 | Harlev et al. |
| 2017/0312025 A1 | 11/2017 | Harlev et al. |
| 2017/0312027 A1 | 11/2017 | Harlev et al. |
| 2018/0001056 A1 | 1/2018 | Leeflang et al. |
| 2018/0042674 A1 | 2/2018 | Mickelsen |
| 2018/0042675 A1 | 2/2018 | Long |
| 2018/0043153 A1 | 2/2018 | Viswanathan et al. |
| 2018/0064488 A1 | 3/2018 | Long et al. |
| 2018/0078170 A1 | 3/2018 | Panescu et al. |
| 2018/0085160 A1 | 3/2018 | Viswanathan et al. |
| 2018/0093088 A1 | 4/2018 | Mickelsen |
| 2018/0133460 A1 | 5/2018 | Townley et al. |
| 2018/0145595 A1* | 5/2018 | Fontana ................. H02M 1/42 |
| 2018/0168511 A1 | 6/2018 | Hall et al. |
| 2018/0184982 A1 | 7/2018 | Basu et al. |
| 2018/0193090 A1 | 7/2018 | de la Rama et al. |
| 2018/0200497 A1 | 7/2018 | Mickelsen |
| 2018/0214195 A1 | 8/2018 | Fraasch et al. |
| 2018/0214202 A1 | 8/2018 | Howard et al. |
| 2018/0221078 A1 | 8/2018 | Howard et al. |
| 2018/0221085 A1* | 8/2018 | Blanck ................. A61B 5/4836 |
| 2018/0243558 A1 | 8/2018 | Athos et al. |
| 2018/0250508 A1 | 9/2018 | Howard |
| 2018/0289417 A1 | 10/2018 | Schweitzer et al. |
| 2018/0303488 A1 | 10/2018 | Hill |
| 2018/0303543 A1 | 10/2018 | Stewart et al. |
| 2018/0311497 A1 | 11/2018 | Viswanathan et al. |
| 2018/0344393 A1 | 12/2018 | Gruba et al. |
| 2018/0360534 A1 | 12/2018 | Teplitsky et al. |
| 2019/0038171 A1 | 2/2019 | Howard |
| 2019/0060632 A1* | 2/2019 | Asirvatham ......... A61B 5/0472 |
| 2019/0069950 A1 | 3/2019 | Viswanathan et al. |
| 2019/0125439 A1 | 5/2019 | Rohl et al. |
| 2019/0151015 A1 | 5/2019 | Viswanathan et al. |
| 2019/0183378 A1 | 6/2019 | Mosesov et al. |
| 2019/0192223 A1 | 6/2019 | Rankin |
| 2019/0201089 A1 | 7/2019 | Waldstreicher et al. |
| 2019/0209238 A1 | 7/2019 | Jimenez |
| 2019/0223938 A1 | 7/2019 | Arena et al. |
| 2019/0223950 A1 | 7/2019 | Gelbart et al. |
| 2019/0231421 A1 | 8/2019 | Viswanathan et al. |
| 2019/0231425 A1 | 8/2019 | Waldstreicher et al. |
| 2019/0233809 A1 | 8/2019 | Neal, II et al. |
| 2019/0256839 A1 | 8/2019 | Neal, II et al. |
| 2019/0269912 A1 | 9/2019 | Viswanathan et al. |
| 2019/0328445 A1 | 10/2019 | Sano et al. |
| 2019/0336198 A1 | 11/2019 | Viswanathan et al. |
| 2019/0336207 A1 | 11/2019 | Viswanathan |
| 2019/0350647 A1 | 11/2019 | Ramberg et al. |
| 2019/0376055 A1 | 12/2019 | Davalos et al. |
| 2020/0129233 A1 | 4/2020 | Viswanathan et al. |
| 2020/0139114 A1 | 5/2020 | Viswanathan et al. |
| 2020/0230403 A1 | 7/2020 | Bowers |

FOREIGN PATENT DOCUMENTS

| | | |
|---|---|---|
| EP | 1125549 | 8/2001 |
| EP | 0797956 | 6/2003 |
| EP | 1127552 | 6/2006 |
| EP | 1340469 | 3/2007 |
| EP | 1009303 | 6/2009 |
| EP | 2213729 | 8/2010 |
| EP | 2425871 | 3/2012 |
| EP | 1803411 | 8/2012 |
| EP | 2532320 A2 | 12/2012 |
| EP | 2587275 | 5/2013 |
| EP | 2663227 | 11/2013 |
| EP | 1909678 | 1/2014 |
| EP | 2217165 | 3/2014 |
| EP | 2376193 | 3/2014 |
| EP | 2708181 | 3/2014 |
| EP | 2777579 A1 | 9/2014 |
| EP | 2934307 | 10/2015 |
| EP | 2777585 | 6/2016 |
| EP | 3287090 A1 | 2/2018 |
| EP | 2382935 B1 | 3/2018 |
| EP | 3111871 B1 | 3/2018 |
| EP | 3151773 B1 | 4/2018 |
| EP | 3056242 B1 | 7/2018 |
| JP | H06-507797 | 9/1994 |
| JP | H10-510745 | 10/1998 |
| JP | 2000-508196 | 7/2000 |
| JP | 2005-516666 | 6/2005 |
| JP | 2006-506184 | 2/2006 |
| JP | 2007-325935 | 12/2007 |
| JP | 2008-538997 | 11/2008 |
| JP | 2009-500129 | 1/2009 |
| JP | 2011-509158 | 3/2011 |
| JP | 2012-050538 | 3/2012 |
| JP | 2015-524732 | 8/2015 |
| JP | 2015-532604 | 11/2015 |
| WO | WO 92/07622 | 5/1992 |
| WO | WO 92/21278 | 12/1992 |
| WO | WO 92/21285 | 12/1992 |
| WO | WO 94/07413 | 4/1994 |
| WO | WO 97/24073 | 7/1997 |
| WO | WO 97/25917 | 7/1997 |
| WO | WO 97/37719 | 10/1997 |
| WO | WO 1999/004851 | 2/1999 |
| WO | WO 1999/022659 | 5/1999 |
| WO | WO 1999/056650 | 11/1999 |
| WO | WO 1999/059486 | 11/1999 |
| WO | WO 2002/056782 | 7/2002 |
| WO | WO 2003/053289 | 7/2003 |
| WO | WO 2003/065916 | 8/2003 |

(56) References Cited

FOREIGN PATENT DOCUMENTS

| | | |
|---|---|---|
| WO | WO 2004/045442 | 6/2004 |
| WO | WO 2004/086994 | 10/2004 |
| WO | WO 2005/046487 | 5/2005 |
| WO | WO 2006/115902 | 11/2006 |
| WO | WO 2007/006055 | 1/2007 |
| WO | WO 2007/079438 | 7/2007 |
| WO | WO 2009/082710 | 7/2009 |
| WO | WO 2009/089343 | 7/2009 |
| WO | WO 2009/137800 | 11/2009 |
| WO | WO 2010/014480 | 2/2010 |
| WO | WO 2011/028310 | 3/2011 |
| WO | WO 2011/154805 | 12/2011 |
| WO | WO 2012/051433 | 4/2012 |
| WO | WO 2012/153928 | 11/2012 |
| WO | WO 2013/019385 | 2/2013 |
| WO | WO 2014/025394 | 2/2014 |
| WO | WO 2014/031800 | 2/2014 |
| WO | WO 2014/036439 | 3/2014 |
| WO | WO 2014/160832 | 10/2014 |
| WO | WO 2015/066322 | 5/2015 |
| WO | WO 2015/099786 | 7/2015 |
| WO | WO 2015/103530 | 7/2015 |
| WO | WO 2015/103574 | 7/2015 |
| WO | WO 2015/130824 | 9/2015 |
| WO | WO 2015/140741 | 9/2015 |
| WO | WO 2015/143327 | 9/2015 |
| WO | WO 2015/171921 | 11/2015 |
| WO | WO 2015/175944 | 11/2015 |
| WO | WO 2015/192018 | 12/2015 |
| WO | WO 2015/192027 | 12/2015 |
| WO | WO 2016/059027 | 4/2016 |
| WO | WO 2016/060983 | 4/2016 |
| WO | WO 2016/081650 | 5/2016 |
| WO | WO 2016/090175 | 6/2016 |
| WO | WO 2017/024123 | 2/2017 |
| WO | WO 2017/093926 | 6/2017 |
| WO | WO 2017/119934 | 7/2017 |
| WO | WO 2017/120169 | 7/2017 |
| WO | WO 2017/192477 | 11/2017 |
| WO | WO 2017/192495 | 11/2017 |
| WO | WO 2017/218734 | 12/2017 |
| WO | WO 2018/005511 | 1/2018 |
| WO | WO 2018/200800 | 11/2018 |
| WO | WO 2018/208795 | 11/2018 |
| WO | WO 2019/118436 | 6/2019 |
| WO | WO 2019/133606 | 7/2019 |
| WO | WO 2019/133608 | 7/2019 |
| WO | WO 2019/147832 | 8/2019 |
| WO | WO 2019/152986 | 8/2019 |
| WO | WO 2019/173309 | 9/2019 |
| WO | WO 2019/217317 | 11/2019 |
| WO | WO 2019/217433 | 11/2019 |

OTHER PUBLICATIONS

Supplementary European Search Report for European Application No. 13827672.0, dated Jul. 11, 2016, 12 pages.
Office Action for European Application No. 13827672.0, dated Feb. 5, 2018, 6 pages.
Notice of Reasons for Rejection for Japanese Application No. 2015-526522, dated Mar. 6, 2017, 3 pages.
Office Action for U.S. Appl. No. 14/400,455, dated Mar. 30, 2017, 10 pages.
International Search Report and Written Opinion for International Application No. PCT/US2013/031252, dated Jul. 19, 2013, 12 pages.
Office Action for U.S. Appl. No. 15/819,726, dated Jun. 4, 2018, 17 pages.
Office Action for U.S. Appl. No. 15/917,194, dated Jun. 4, 2018, 17 pages.
Office Action for U.S. Appl. No. 15/917,194, dated Oct. 9, 2018, 13 pages.
First Office Action for Chinese Application No. 201580006848.8, dated Jan. 29, 2018, 15 pages.
Office Action for U.S. Appl. No. 15/201,997, dated Dec. 17, 2018, 17 pages.
International Search Report and Written Opinion for International Application No. PCT/US2018/050660, dated Nov. 26, 2018, 13 pages.
Office Action for European Application No. 15701856.5, dated Dec. 11, 2017, 6 pages.
Notice of Reasons for Rejection for Japanese Application No. 2016-544072, dated Oct. 1, 2018, 11 pages.
International Search Report and Written Opinion for International Application No. PCT/US2015/010138, dated Mar. 26, 2015, 14 pages.
International Preliminary Report on Patentability for International Application No. PCT/US2015/010138, dated Jul. 12, 2016, 9 pages.
Supplementary European Search Report for European Application No. 15733297.4, dated Aug. 10, 2017, 7 pages.
Office Action for U.S. Appl. No. 15/201,997, dated Apr. 3, 2017, 6 pages.
Office Action for U.S. Appl. No. 15/201,997, dated Aug. 29, 2017, 12 pages.
Office Action for U.S. Appl. No. 15/201,997, dated Jul. 12, 2018, 12 pages.
International Search Report and Written Opinion for International Application No. PCT/US2015/010223, dated Apr. 10, 2015, 19 pages.
International Preliminary Report on Patentability for International Application No. PCT/US2015/010223, dated Jul. 12, 2016, 12 pages.
International Search Report and Written Opinion for International Application No. PCT/US2015/029734, dated Nov. 24, 2015, 15 pages.
Office Action for U.S. Appl. No. 15/795,062, dated Dec. 19, 2017, 14 pages.
Office Action for U.S. Appl. No. 15/795,062, dated Apr. 9, 2018, 20 pages.
International Search Report and Written Opinion for International Application No. PCT/US2015/031086, dated Oct. 21, 2015, 16 pages.
Office Action for U.S. Appl. No. 15/795,075, dated Feb. 6, 2018, 9 pages.
Office Action for U.S. Appl. No. 15/795,075, dated Jun. 15, 2018, 10 pages.
Extended European Search Report for European Application No. 15849844.4, dated May 3, 2018, 8 pages.
International Search Report and Written Opinion for International Application No. PCT/US2015/055105, dated Mar. 1, 2016, 15 pages.
Office Action for U.S. Appl. No. 15/796,255, dated Jan. 10, 2018, 12 pages.
Extended European Search Report for European Application No. 15806855.1, dated Jan. 3, 2018, 8 pages.
International Search Report and Written Opinion for International Application No. PCT/US2015/035582, dated Oct. 2, 2015, 17 pages.
Extended European Search Report for European Application No. 15806278.6, dated Feb. 9, 2018, 5 pages.
International Search Report and Written Opinion for International Application No. PCT/US2015/035592, dated Oct. 2, 2015, 13 pages.
Office Action for U.S. Appl. No. 15/334,646, dated Jul. 25, 2017, 19 pages.
Office Action for U.S. Appl. No. 15/334,646, dated Nov. 16, 2017, 26 pages.
International Search Report and Written Opinion for International Application No. PCT/US2016/057664, dated Feb. 24, 2017, 11 pages.
Office Action for U.S. Appl. No. 15/796,375, dated Jan. 24, 2018, 25 pages.
Office Action for U.S. Appl. No. 15/796,375, dated May 30, 2018, 26 pages.

(56) References Cited

OTHER PUBLICATIONS

Office Action for U.S. Appl. No. 15/796,375, dated Nov. 16, 2018, 27 pages.
International Search Report and Written Opinion for International Application No. PCT/US2017/012099, dated May 18, 2017, 17 pages.
Office Action for U.S. Appl. No. 15/711,266, dated Feb. 23, 2018, 14 pages.
International Search Report and Written Opinion for International Application No. PCT/US2018/029938, dated Aug. 29, 2018, 14 pages.
International Search Report and Written Opinion for International Application No. PCT/US2017/037609, dated Nov. 8, 2017, 13 pages.
Office Action for U.S. Appl. No. 15/672,916, dated Feb. 13, 2018, 16 pages.
Office Action for U.S. Appl. No. 15/672,916, dated Jul. 20, 2018, 23 pages.
Office Action for U.S. Appl. No. 15/499,804, dated Jan. 3, 2018, 20 pages.
Office Action for U.S. Appl. No. 15/794,717, dated Feb. 1, 2018, 10 pages.
International Search Report and Written Opinion for International Application No. PCT/US2018/029552, dated Jun. 29, 2018, 13 pages.
Office Action for U.S. Appl. No. 15/970,404, dated Oct. 9, 2018, 21 pages.
Du Pre, B.C. et al., "Minimal coronary artery damage by myocardial electroporation ablation," Europace, 15(1):144-149 (2013).
Hobbs, E. P., "Investor Relations Update: Tissue Ablation via Irreversible Electroporation (IRE)," Powerpoint (2004), 16 pages.
Lavee, J. et al., "A Novel Nonthermal Energy Source for Surgical Epicardial Atrial Ablation: Irreversible Electroporation," The Heart Surgery Forum #2006-1202, 10(2), 2007 [Epub Mar. 2007].
Madhavan, M. et al., "Novel Percutaneous Epicardial Autonomic Modulation in the Canine for Atrial Fibrillation: Results of an Efficacy and Safety Study," Pace, 00:1-11 (2016).
Neven, K. et al., "Safety and Feasibility of Closed Chest Epicardial Catheter Ablation Using Electroporation," Circ Arrhythm Electrophysiol., 7:913-919 (2014).
Neven, K. et al., "Myocardial Lesion Size After Epicardial Electroporation Catheter Ablation After Subxiphoid Puncture," Circ Arrhythm Electrophysiol., 7(4):728-733 (2014).
Neven, K. et al., "Epicardial linear electroporation ablation and lesion size," Heart Rhythm, 11:1465-1470 (2014).
Van Driel, V.J.H.M. et al., "Pulmonary Vein Stenosis After Catheter Ablation Electroporation Versus Radiofrequency," Circ Arrhythm Electrophysiol., 7(4):734-738 (2014).
Van Driel, V.J.H.M. et al., "Low vulnerability of the right phrenic nerve to electroporation ablation," Heart Rhythm, 12:1838-1844 (2015).
Wittkampf, F.H. et al., "Myocardial Lesion Depth With Circular Electroporation Ablation," Circ. Arrhythm Electrophysiol., 5(3):581-586 (2012).
Wittkampf, F.H. et al., "Feasibility of Electroporation for the Creation of Pulmonary Vein Ostial Lesions," J Cardiovasc Electrophysiol, 22(3):302-309 (Mar. 2011).
Office Action for Canadian Application No. 2,881,462, dated Mar. 19, 2019, 5 pages.
Office Action for Japanese Application No. 2018-036714, dated Jan. 16, 2019, 8 pages.
Office Action for U.S. Appl. No. 15/201,983, dated Apr. 3, 2019, 16 pages.
Office Action for U.S. Appl. No. 15/341,523, dated Jan. 29, 2019, 10 pages.
Office Action for U.S. Appl. No. 15/795,075, dated Apr. 10, 2019, 11 pages.
Office Action for U.S. Appl. No. 15/672,916, dated Apr. 9, 2019, 31 pages.
Partial European Search Report for European Application No. 18170210.1, dated Feb. 14, 2019, 13 pages.
Office Action for U.S. Appl. No. 15/970,404, dated Apr. 12, 2019, 20 pages.
Office Action for U.S. Appl. No. 15/917,194, dated Apr. 29, 2019, 10 pages.
Office Action for U.S. Appl. No. 15/795,062, dated May 3, 2019, 21 pages.
International Search Report and Written Opinion for International Application No. PCT/US2019/014226, dated Apr. 29, 2019, 15 pages.
Extended European Search Report for European Application No. 18189811.5, dated May 14, 2019, 7 pages.
International Search Report and Written Opinion for International Application No. PCT/US2019/017322, dated May 10, 2019, 15 pages.
Office Action for U.S. Appl. No. 15/341,512, dated Aug. 1, 2019, 19 pages.
Office Action for U.S. Appl. No. 15/341,523, dated Jul. 30, 2019, 8 pages.
Office Action for U.S. Appl. No. 15/795,075, dated Jul. 31, 2019, 12 pages.
Office Action for U.S. Appl. No. 15/484,969, dated Sep. 4, 2019, 12 pages.
Office Action for U.S. Appl. No. 15/354,475, dated May 23, 2019, 7 pages.
Extended European Search Report for European Application No. 16884132.8, dated Jul. 8, 2019, 7 pages.
Office Action for U.S. Appl. No. 16/416,677, dated Aug. 15, 2019, 8 pages.
Extended European Search Report for European Application No. 17736218.3 dated Aug. 23, 2019, 9 pages.
Office Action for U.S. Appl. No. 16/181,027, dated Sep. 4, 2019, 12 pages.
Office Action for U.S. Appl. No. 16/240,066, dated May 29, 2019, 7 pages.
Extended European Search Report for European Application No. 18170210.1, dated May 17, 2019, 11 pages.
International Search Report and Written Opinion for International Application No. PCT/US2019/030922, dated Sep. 6, 2019, 12 pages.
International Search Report and Written Opinion for International Application No. PCT/US2019/030882, dated Sep. 10, 2019, 17 pages.
Office Action for U.S. Appl. No. 16/405,515, dated Sep. 6, 2019, 9 pages.
International Search Report and Written Opinion for International Application No. PCT/US2019/031135, dated Aug. 5, 2019, 11 pages.
International Search Report and Written Opinion for International Application No. PCT/US2019/028943, dated Sep. 17, 2019, 17 pages.
Office Action for U.S. Appl. No. 15/201,983, dated Nov. 15, 2019, 15 pages.
Office Action for U.S. Appl. No. 15/341,512, dated Nov. 12, 2019, 18 pages.
Office Action for U.S. Appl. No. 15/795,062, dated Nov. 4, 2019, 23 pages.
Office Action for U.S. Appl. No. 16/375,561, dated Oct. 17, 2019, 15 pages.
Office Action for U.S. Appl. No. 15/970,404, dated Nov. 12, 2019, 19 pages.
Extended European Search Report for European Application No. 19182099.2, dated Dec. 13, 2019, 7 pages.
Office Action for Japanese Application No. 2018-036714, dated Nov. 27, 2019, 5 pages.
Office Action for U.S. Appl. No. 15/917,194, dated Dec. 20, 2019, 10 pages.
Office Action for U.S. Appl. No. 16/722,650, dated Mar. 25, 2020, 12 pages.
Office Action for U.S. Appl. No. 16/573,704, dated Dec. 17, 2019, 6 pages.

(56) References Cited

OTHER PUBLICATIONS

Office Action for U.S. Appl. No. 16/741,506, dated Feb. 28, 2020, 5 pages.
Office Action for U.S. Appl. No. 16/723,407, dated Mar. 19, 2020, 13 pages.
Office Action for U.S. Appl. No. 16/785,392, dated May 29, 2020, 18 pages.
Tekle, E. et al., "Electroporation by using bipolar oscillating electric field: An improved method for DNA transfection of NIH 3T3 cells," Proc. Natl. Acad. Sci. USA, vol. 88, pp. 4230-4234, May 1991.
First Office Action for Chinese Application No. 201680077941.2, dated Jun. 30, 2020, 13 pages.
Notice of Reasons for Rejection for Japanese Application No. 2018-534869, dated Jul. 29, 2020, 11 pages.
International Search Report and Written Opinion for International Application No. PCT/US2020/061564, dated Mar. 12, 2021, 14 pages.

\* cited by examiner

SYSTEMS, APPARATUSES, AND METHODS FOR PROTECTING ELECTRONIC COMPONENTS FROM HIGH POWER NOISE INDUCED BY HIGH VOLTAGE PULSES

TECHNICAL FIELD

The embodiments described herein relate generally to medical devices for therapeutic electrical energy delivery, and more particularly to systems, apparatuses, and methods for protecting electronic components (e.g., sensitive equipment or circuitry) during pulsed electric field ablation procedures.

BACKGROUND

Application of brief ultra-short high voltage pulses to tissue may generate high electric fields in tissue to generate a local region of ablated tissue by the biophysical mechanism of irreversible electroporation. In applications including cardiac applications, high voltage pulses may be applied in synchrony with a cardiac cycle of a subject. For example, high voltage pulses can be applied during specific periods of the cardiac cycle (e.g., refractory cycle of the cardiac chambers), thereby avoiding the risk of induced arrhythmias such as ventricular fibrillation. In some applications, to ensure synchrony of pulsed field ablation pulses with the cardiac cycle, a cardiac stimulator can be used to pace or stimulate the cardiac chamber(s) with a regular cycle of periodic pacing signals having a well-defined time period to establish periodicity of electrocardiogram (ECG) activity of the heart. Other devices, e.g., sensing and/or mapping systems, can also be used to monitor a subject's cardiac cycle or detail a subject's cardiac activity. A cardiac stimulator may also be used in clinical procedures where a pacing function is required to maintain periodic and regular electrical activity in the cardiac chambers during at least a portion of the procedure. The cardiac stimulator and these other devices can use intracardiac devices (e.g., catheters) that can be suitably positioned in one or more cardiac chamber(s) to deliver signals to or receive signals from the heart, or external surface patches or surface leads to record patient surface ECG recordings. When these devices are used during a pulsed electric field ablation procedure, however, they can become exposed to high voltages. Such exposure can result in large, generally unbalanced, currents, and/or large common mode voltages with respect to earth ground, being induced in the electrodes or leads of the intracardiac catheters. The large unbalanced currents and/or voltages can span a band of frequencies and disrupt the operation of the cardiac stimulator and/or these other devices, thus interrupting pacing, sensing, mapping, magnetic sensor operation, and/or pulsed field ablation functions. The disruption may be due to a hardware response to the voltages and currents, or due to the equipment actively monitoring the patient for anomalous signals for safety reasons.

Accordingly, it can be desirable to have systems, apparatuses, and methods for addressing this issue.

SUMMARY

Described herein are systems, devices, and methods for protecting electronic components (e.g., circuitry, devices, and/or other components) from induced currents and high voltage exposure during pulsed electric field ablation procedures.

In some embodiments, the ablation devices used in these systems may be deployed epicardially or endocardially in cardiac applications. The pulsed waveforms may include predetermined parameters or may be automatically generated by a signal generator.

In some embodiments, a system can include a first set of electrodes and a second set of electrodes. Generally, the second set of electrodes can be disposed near cardiac tissue of a heart, or they can be part of surface patches or similar external recording or monitoring devices. A signal generator may be configured to generate a pulse waveform. The signal generator may be coupled to the first set of electrodes and in some embodiments can be configured to repeatedly deliver the pulse waveform to the first set of electrodes in synchrony with a set of cardiac cycles of the heart. In other embodiments, the signal generator can be configured to repeatedly deliver the pulse waveform to the first set of electrodes without synchrony being established with the cardiac cycle. In this latter case, it can still be useful to protect other electronic components (e.g., lab equipment such as cardiac stimulators (used generally for pacing functions), mapping systems, magnetic tracking equipment, imaging equipment, etc.). The first set of electrodes may be configured to generate a pulsed electric field in response to the delivery of the pulse waveform to ablate the cardiac tissue. A protection device may be configured to selectively couple and decouple an electronic device to the second set of the electrodes. A control element (e.g., processor, switch, control signal) may be coupled to the protection device and configured to control the protection device to decouple the electronic device from the second set of electrodes during intervals of time beginning before and ending after each delivery of the pulse waveform to the first set of electrodes.

In some embodiments, an apparatus may include a first set of electrodes disposable near cardiac tissue of a heart. A signal generator may be coupled to the first set of electrodes and configured to generate a pulse waveform. A switch component may be coupled to the signal generator. The switch component may be configured to switch between a conducting state in which an electronic device is coupled to a second set of electrodes and a non-conducting state in which an electronic device is decoupled from the second set of electrodes. The second set of electrodes may be disposable near the first set of electrodes, or generally in a cardiac or anatomical chamber, or it may be disposed on or near the external surface of the subject. A processor may be coupled to the switch component. The processor may be configured to receive trigger signals, each trigger signal associated with a cardiac cycle of the heart or with an ablation output from the signal generator. In response to receiving each trigger signal, the processor may be configured to set the switch component to the non-conducting state such that the electronic device is decoupled from the second set of electrodes. The processor may be configured to deliver, from the signal generator and after setting the switch component to the non-conducting state, the pulse waveform to the first set of electrodes such that the first set of electrodes generates a pulsed electric field. The processor may be configured to set, after delivering the pulse waveform, the switch component to the conducting state such that the electronic device is coupled to the second set of electrodes. In some embodiments, a control signal being coupled to the switch component can set the state of the switch to perform the functions described above.

In some embodiments, a method may include delivering pacing signals to a heart by a second set of electrodes positioned near cardiac tissue of the heart. After delivery of each pacing signal to the heart, the switch component being selectively able to couple to an electronic device may be set to be in a non-conductive state such that the second set of electrodes is decoupled from the electronic device. After setting the switch component to be in the non-conductive state, a pulse waveform may be delivered to a first set of electrodes positioned near cardiac tissue of the heart such that the first set of electrodes generates a pulsed electric field for ablating the cardiac tissue. After delivering the pulse waveform, the switch component may be set to be in a conductive state such that the second set of electrodes is coupled to the electronic device.

BRIEF DESCRIPTION OF THE DRAWINGS

FIG. 3B is a schematic diagram of a system for protecting electronic components from high voltage signals, according to embodiments, including externally and/or internally disposed electrodes that may be connected to a variety of medical equipment, including but not limited to cardiac stimulators, ECG recording systems, ECG or other patient data monitoring systems, electroanatomical mapping systems, device navigation/tracking systems, combinations thereof, and the like.

DETAILED DESCRIPTION

Described herein are systems, devices, and methods for protecting circuits from high power noise induced during pulsed electric field ablation. Pulsed electric field ablation uses ultra-short high-voltage pulses to generate large electric fields at desired regions of interest to generate a local region of ablated tissue via irreversible electroporation. In certain applications, including cardiac applications, it can be desirable to generate pulses for pulsed electric field ablation in synchronicity with a cardiac cycle. Synchronizing ablation energy delivery with the cardiac cycle may reduce the risk of induced arrhythmias such as atrial and/or ventricular fibrillation. One method of synchronizing delivery of pulses can be to pace or stimulate one or more cardiac chambers with periodic pacing signals with a predefined time period. For example, a cardiac stimulator may be used to deliver pacing pulses to one or more cardiac chambers such that the cardiac rhythm of a patient synchronizes with the pacing pulse.

Figure 1:
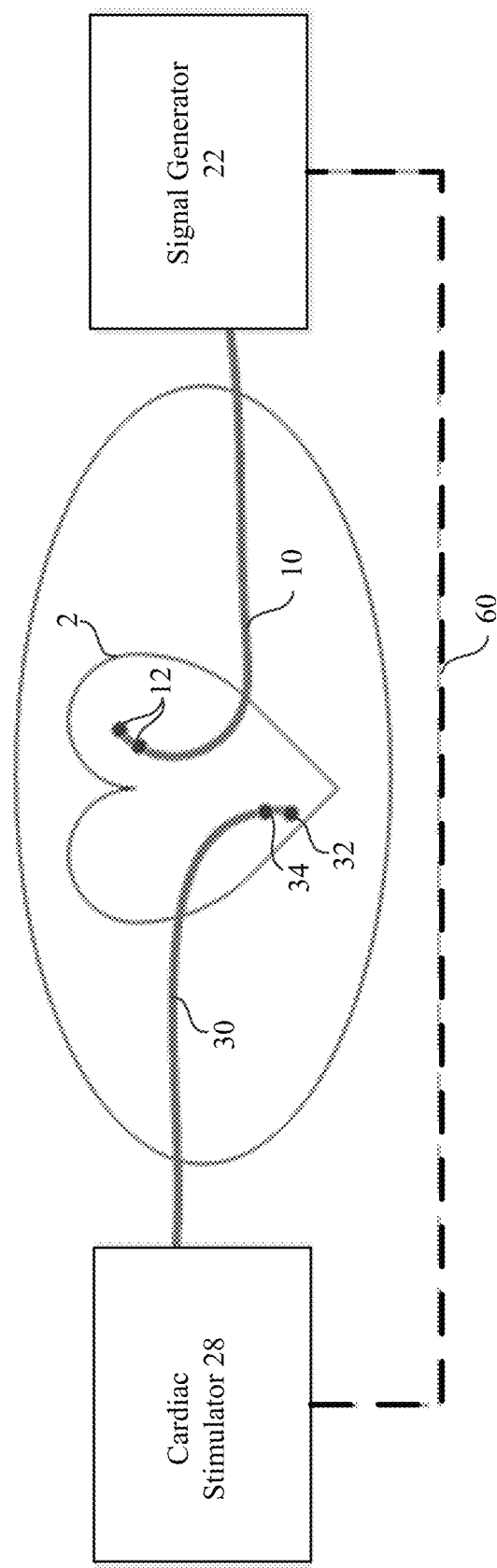
FIG. 1 is a schematic diagram of components of a signal generator and a cardiac stimulator being disposed in a heart, according to embodiments.

In some embodiments, pacing pulses can be delivered to the cardiac chamber(s) via an intracardiac catheter that is suitably positioned in the chamber(s). For example, FIG. 1 depicts a cardiac stimulator (28) that is coupled to an intracardiac catheter (30) suitable positioned in a chamber of a heart (2). The catheter (30) can have one or more electrodes (32, 34) that are used to conduct a pacing signal into the heart. In an embodiment, a pair of electrodes on the catheter (30) (e.g., a most distal electrode (32) and an electrode (34) immediately proximal to the most distal electrode (32)) can be used as a bipolar pair to deliver the pacing signal, thus providing forward and return current paths for the pacing signal. The cardiac chamber responds to the pacing pulse (referred to herein as "pacing capture") by timing its ECG signal generation (e.g., the QRS waveform) to synchronize with the pacing pulse. Accordingly, periodicity of the ECG activity of the heart can be established. Once such periodicity is established and confirmed by the physician (e.g., from displayed ECG activity obtained, for example, for a variety of recording or sensing electrodes), the delivery of the pulsed field ablation pulses can be timed to start in synchrony with the pacing pulses, including any predetermined offsets, and delivery can be completed within refractory windows following the QRS waveform of an ECG signal.

In cardiac applications, pulsed field ablation energy can be delivered through a customized ablation catheter including a plurality of electrodes. For example, as depicted in FIG. 1, a signal generator (22) (e.g., a pulsed field ablation pulse generator) can be coupled to an ablation catheter (10) with electrodes (12) that are suitably disposed in the heart (2). The delivery of the pulsed field ablation voltage pulses can be synchronized with the delivery of the pacing signals with appropriate offsets, as indicated by (60). Since the pacing catheter (30) can be located in the cardiac environment as well (e.g., in the same or a nearby chamber of the heart (2)), high voltage pulse waveforms applied to heart tissue may couple to the pacing catheter (30) and induce currents in one or more of the pacing catheter (30) and devices coupled thereto (e.g., cardiac stimulator (28)).

During normal delivery of pacing pulses, the forward and return currents of the electrodes (32, 34) of the pacing catheter (30) are balanced (e.g., equal in magnitude and opposite in direction). However, electrical coupling of the high voltage ablation energy to the pacing catheter (30) may induce large and generally unbalanced currents and/or common mode voltages in the leads of the pacing catheter (30). These large unbalanced currents and/or voltages can span a band of frequencies and can disrupt the operation of the pacing system or cardiac stimulator (28) or other electronic equipment coupled thereto. For example, the large voltage exposure of the pacing catheter (30) may exceed the common-mode rejection of the cardiac stimulator (28) and cause system failure and/or reset of the stimulator (which can be either pacing for synchronized delivery of ablation or pacing the cardiac chamber(s) for other medical reasons). The high voltage levels and high currents associated with the induced noise imply a large power level for the noise and can lead to unwanted effects.

Figure 2:
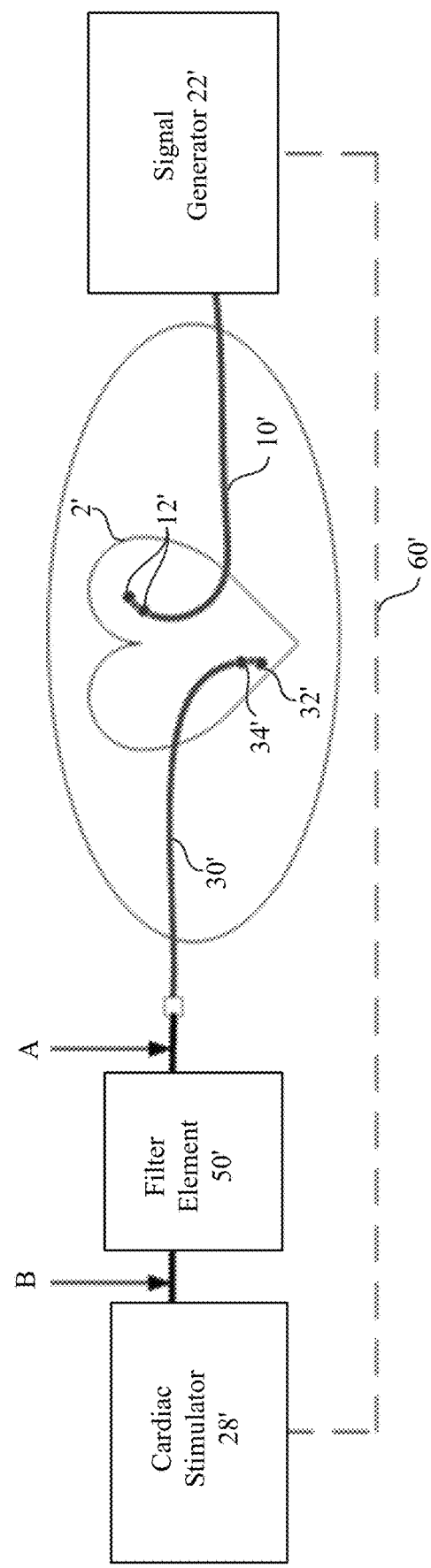
FIG. 2 is a schematic diagram of components of a signal generator and a cardiac stimulator being disposed in a heart, with passive filtering for protection of the cardiac stimulator, according to embodiments.

This high-power induced noise can be difficult to suppress and, therefore, it can be desirable to have systems, devices, and methods for suppressing induced currents in accessory devices in pulsed electric field ablation energy delivery applications. In some embodiments, currents induced by pulsed electric field ablation can be suppressed through implementation of passive filtering systems, devices, and methods, as described in U.S. application Ser. No. 62/667,887, filed on May 7, 2018, and titled "SYSTEMS, APPARATUSES, AND METHODS FOR FILTERING HIGH VOLTAGE NOISE INDUCED BY PULSED ELECTRIC FIELD ABLATION," the contents of which are hereby incorporated by reference in its entirety. FIG. 2 depicts an example of a system including passive filtering. A cardiac stimulator (28') can be coupled to a pacing catheter (30') including a plurality of electrodes (32', 34'). A signal generator (22') can be coupled to an ablation catheter (10') including a plurality of electrodes (12'). The electrodes (32', 34') of the pacing catheter (30') can be disposed in a heart (2') along with the electrodes (12') of the ablation catheter (10'). A filter element (50') can be coupled between the cardiac stimulator (28') and the pacing catheter (30'). The filter element (50') can passively filter signals from the pacing catheter (30') prior to those signals being received at the cardiac stimulator (28'), thereby suppressing certain induced currents. For example, at A, long wires can pick up high voltages, while at B, after the passive filtering, residual voltage and current can pass onto the cardiac stimulator (28').

In some instances, however, coupled noise having a large amplitude (e.g., large voltage spikes) can be difficult to reject using passive filtering techniques and therefore faults and/or resets of equipment including a cardiac stimulator can still occur. Commercially available stimulators can also include different design parameters such that one level of protection may be sufficient for one type of stimulator while being insufficient for a second type of stimulator.

Systems, devices, and methods disclosed herein provide protection for sensitive electronics and ancillary devices in pulsed electric field ablation applications using actively driven rapid switching of signal paths. In some embodiments, a protection device may be coupled to the pacing device to actively and selectively electrically isolate the pacing device from the other electronic components of the ablation system. In particular, the pacing device may be electrically isolated from the system during a predetermined time period corresponding to delivery of the pulse waveform to tissue. Electrical connection may be reestablished to enable operation of the pacing device between periods of high voltage energy delivery. In some embodiments, the protection device may include a high speed switch coupled between the ablation system and pacing device. Consequently, components of the system such as the cardiac stimulator may be protected from currents that may be induced in the pacing device by the high voltage pulse waveforms applied by the ablation device. Additionally or alternatively, the protection device may further provide passive circuit protection.

In some embodiments, sensitive circuitry or a piece of ancillary equipment (e.g., a cardiac stimulator, electroanatomical mapping system, ECG recording or monitoring system, etc.) can be protected from high voltage pulsed field ablation signals present in a subject by having such circuitry or equipment be electrically isolated. Electrical isolation can be implemented manually by disconnecting conductors between the circuitry or equipment can the subject, but a manual approach may not be possible in certain instances. For example, for certain types of equipment that serve repeated function, e.g., a cardiac stimulator that is intended to provide ongoing pacing of a subject's heart during a pulsed field ablation procedure, it is necessary for physical connections between the equipment and the subject to remain intact. In these instances, it can be desirable to accomplish physical disconnection using electronic components. For example, electronic components can be used to provide bi-directional open circuit isolation between the subject and protected ancillary equipment for certain time intervals during which a high voltage is present and re-establish connections during other time intervals to otherwise allow for intended functioning of the equipment.

The term "electroporation" as used herein refers to the application of an electric field to a cell membrane to change the permeability of the cell membrane to the extracellular environment. The term "reversible electroporation" as used herein refers to the application of an electric field to a cell membrane to temporarily change the permeability of the cell membrane to the extracellular environment. For example, a cell undergoing reversible electroporation can observe the temporary and/or intermittent formation of one or more pores in its cell membrane that close up upon removal of the electric field. The term "irreversible electroporation" as used herein refers to the application of an electric field to a cell membrane to permanently change the permeability of the cell membrane to the extracellular environment. For example, a cell undergoing irreversible electroporation can observe the formation of one or more pores in its cell membrane that persist upon removal of the electric field.

Pulse waveforms for electroporation energy delivery as disclosed herein may enhance the safety, efficiency, and effectiveness of energy delivery to tissue by reducing the electric field threshold associated with irreversible electroporation, thus yielding more effective ablative lesions with a reduction in total energy delivered. In some embodiments, the voltage pulse waveforms disclosed herein may be hierarchical and have a nested structure. For example, the pulse waveform may include hierarchical groupings of pulses having associated timescales. In some embodiments, the methods, systems, and devices disclosed herein may comprise one or more of the methods, systems, and devices described in International Application Serial No. PCT/US2019/014226, filed on Jan. 18, 2019, published as International Publication No. WO/2019/143960 on Jul. 25, 2019, and titled "SYSTEMS, DEVICES AND METHODS FOR FOCAL ABLATION," the contents of which are hereby incorporated by reference in its entirety.

Systems

Disclosed herein are systems and devices configured for suppressing induced currents in connection with tissue ablation. Generally, a system described here for ablating tissue with high voltage pulse waveforms may include a cardiac stimulator for generating a cardiac pacing signal delivered by a pacing device to the heart. The cardiac pacing signal is used to synchronize delivery of a pulse waveform generated by a signal generator, and the pulse waveform is delivered using an ablation device having one or more electrodes. In another embodiment, the ablation with high voltage pulse waveforms can be performed asynchronously (i.e., without synchronizing with cardiac stimulation). It is generally desirable in these embodiments also to protect other electronic equipment such as cardiac stimulators, electroanatomical mapping systems, device navigation/tracking systems, ECG recording or monitoring systems etc. that may be connected to the patient via device electrodes that are placed either internally in the patient or externally on the patient or attached to the patient surface (for example, needle electrodes, pacing leads etc.). Thus, the systems, methods and implementations described in the present disclosure apply to asynchronous ablation delivery. Furthermore, as described herein, the systems and devices may be deployed epicardially and/or endocardially to treat atrial fibrillation. Voltages may be applied to a selected subset of the electrodes, with independent subset selections for anode and cathode electrode selections.

Figure 3A:
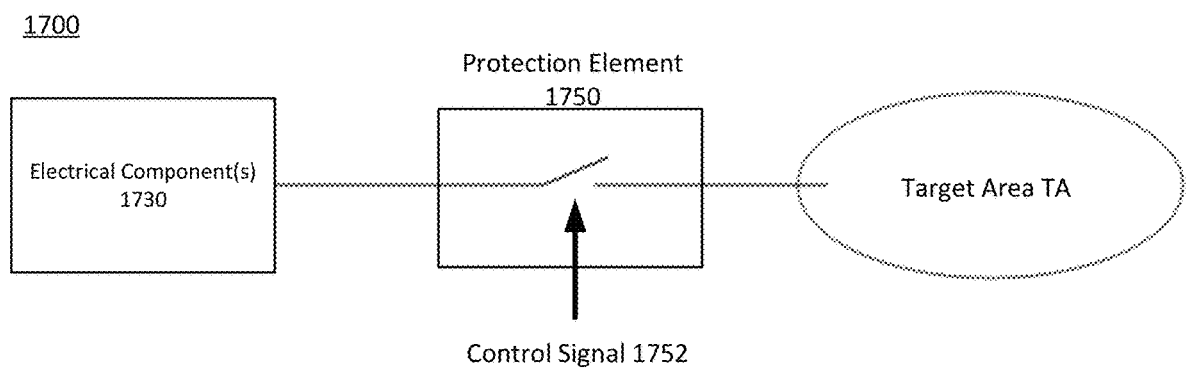
FIG. 3A is a schematic diagram of a system for protecting electronic components from high voltage signals, according to embodiments.

FIG. 3A illustrates an example system (1700) including an integrated protection element (1750). The protection element (1750) can be situated between electrical components (1730) and a target area (TA) (e.g., a heart of a patient). The protection element (1750) can be configured with a voltage rating corresponding to an anticipated exposure voltage on the patient side of a pulsed electric field ablation procedure, which can be a few thousand volts. The protection element (1750) can function as an isolation component that is configured to transition to an open circuit configuration and back to a closed circuit configuration based on a control signal. The protection element (1750) is configured to respond quickly (e.g., quickly switch between its open and closed configurations) to reduce the open-circuit duty cycle, such that the protection element (1750) can electrically isolate certain electrical components (1730) for the duration of a high-voltage exposure but otherwise connect those electrical components to the target area (TA).

Examples of suitable protection elements (1750) include electro-mechanical relays (e.g., reed relays), solid-state relays, and/or high-voltage metal-oxide semiconductor field-effect transistor (MOSFET) devices. Reed relays can be a less suitable option for isolation component implementation, as such relays act slower than other types of protection devices and are susceptible to damage/contact fusing if switched during exposure to high currents. When the system (1700) is used with the protection element (1750) implemented as a reed relay, the coordination and timing of the system (1700) need to be adjusted to handle the slower reaction time of such relays. A preferred implementation of a protection element (1750) is with two back-to-back MOSFETs with common source terminals, as further described with reference to FIG. 5 below.

Figure 3B:
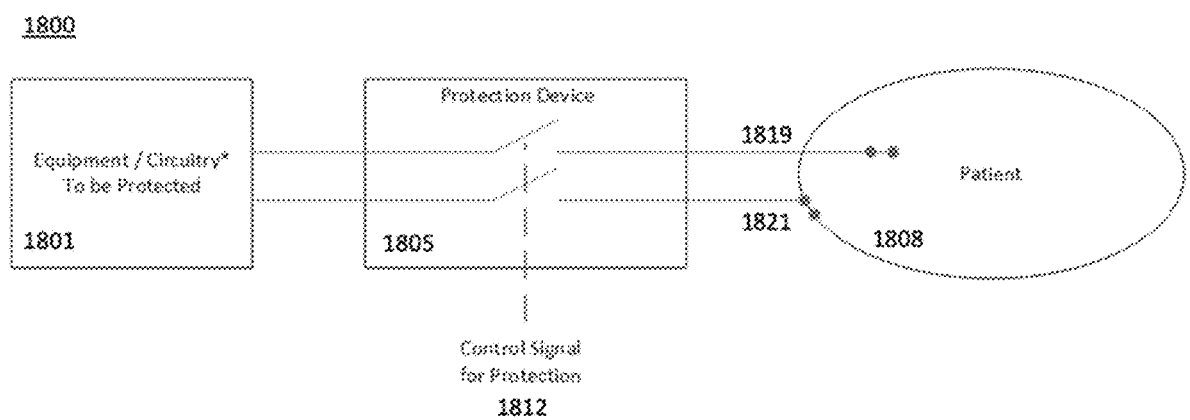

FIG. 3B illustrates an example system (1800) including an integrated protection element (1805). The protection element (1805) can be situated between electrical components (1801) and patient anatomy (1808). The protection element (1805) can be configured with a voltage rating corresponding to an anticipated exposure voltage on the patient side of a pulsed electric field ablation procedure, which can be a few thousand volts. Such high voltage exposure can occur via internally placed (with respect to patient) device electrodes (1819) or externally placed/mounted (on the patient surface) electrodes (1821). Such electrodes in general can connect to a variety of medical electronic equipment, including but not limited to electroanatomical mapping systems, device navigation/tracking systems, ECG recording/monitoring systems, combinations thereof, and the like that can generally be in use in a clinical laboratory or procedure room. The protection element (1805) can function as an isolation component that is configured to transition to an open circuit configuration and back to a closed circuit configuration based on a control signal (1812). The protection element (1805) is configured to respond quickly (e.g., quickly switch between its open and closed configurations) to reduce the open-circuit duty cycle, such that the protection element (1805) can electrically isolate electrical components (1801) such as those described above for the duration of a high-voltage exposure but otherwise connect those electrical components to the patient anatomy (1808).

Examples of suitable protection elements (1805) include electro-mechanical relays (e.g., reed relays), solid-state relays, and/or high-voltage metal-oxide semiconductor field-effect transistor (MOSFET) devices. Reed relays can be a less suitable option for isolation component implementation, as such relays act slower than other types of protection devices and are susceptible to damage/contact fusing if switched during exposure to high currents. When the system (1800) is used with the protection element (1805) implemented as a reed relay, the coordination and timing of the system (1800) need to be adjusted to handle the slower reaction time of such relays. In some embodiments, a protection element (1805) can include two back-to-back MOSFETs with common source terminals, as further described with reference to FIG. 5 below.

Figure 4:
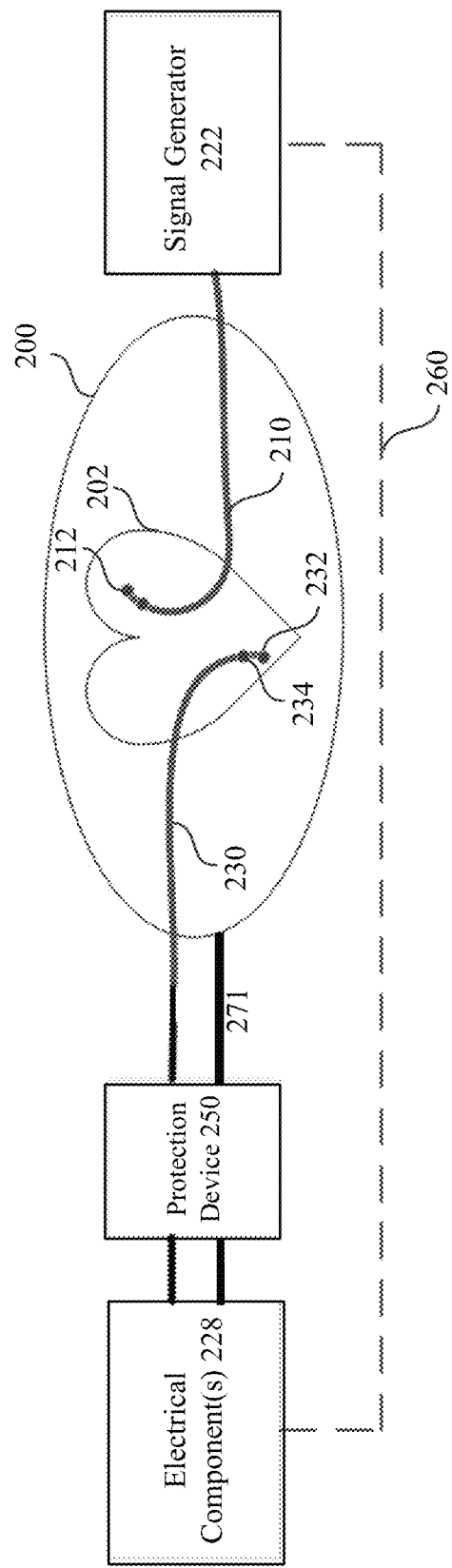
FIG. 4 is a schematic diagram of components of a signal generator and one or more pieces of medical electronic equipment connected to electrodes disposed in a heart/cardiac anatomy or on a patient surface, with a protection device for protection of the medical electronic equipment, according to embodiments.

FIG. 4 is a schematic diagram of an electroporation system disposed in a heart (202) of a patient (200). The electroporation system may include an ablation device (210), signal generator (222), electronic component(s) (e.g., medical electronic equipment) (228), catheter device (230), and protection device (250). In some embodiments, the electronic component(s) (228) may be implemented as a cardiac pacing system (228). The signal generator (222) may be coupled to the ablation device (210) and configured to receive a pacing/synchronization signal (260) generated by the cardiac pacing system (228). The signal generator (222) may be configured to generate ablation pulse waveforms delivered to tissue by electrodes (212) of the ablation device (210). In some embodiments, the catheter device (230) implemented as a pacing device (230) may be configured to pace the heart and measure cardiac activity using respective pacing electrodes (232) and signal electrodes (234). In some embodiments, electrodes (271) may also be placed externally at the patient surface. The protection device (250) may be coupled between the cardiac stimulator (228) and the electrodes (232, 234) of the catheter device (230) or electrodes (271). In some embodiments, the protection device (250) is configured to synchronize electrical isolation of the pacing device (230) with delivery of ablation energy by the ablation device (210).

FIG. 4 is a schematic illustration of an embodiment of an electroporation system including a pacing device (230) (e.g., pacing catheter) and an ablation device (210) (e.g., ablation catheter) disposed in a heart (202). The pacing device (230) may be configured to deliver pacing signal to the heart (202) and the ablation device (210) may be configured to receive a pulse waveform and generate an electric field for ablating cardiac tissue. Pacing device (230) may be introduced into a chamber of the heart (202) (e.g., a right ventricle), or placed in other cardiac anatomy such as in the coronary sinus and positioned such that it can stimulate the heart and obtain pacing capture. The pacing device (230) may comprise electrodes (232, 234), which can be configured to deliver a pacing signal to the heart (202). For example, the electrodes (232, 234) may be configured as a bipolar pair to pace the heart (202) and may be coupled to a cardiac stimulator (e.g., cardiac stimulator (128)). In some embodiments, the pacing device (230), the ablation device (210), and/or another device positioned in the heart can include one or more electrodes (not depicted) for measuring intracardiac activity (e.g., ECG signal) of the heart (202).

In some embodiments, a distal portion of an ablation device (210) may be introduced into an endocardial space of the heart (202) (e.g., a left atrium), e.g., through an atrial septum via a trans-septal puncture. The distal portion of the ablation device (210) may include a set of electrodes (212) configured to deliver ablation energy (e.g., pulse electric field energy) to tissue. For example, the ablation device (210) may be positioned near an inner radial surface of a lumen (e.g., one or more pulmonary vein ostia) (not shown) for delivery of pulse waveforms to ablate tissue. In some embodiments, the electrodes (212) of the ablation device (216) may be a set of independently addressable electrodes. Each electrode may include an insulated electrical lead configured to sustain a voltage potential of at least about 700 V without dielectric breakdown of its corresponding insulation. In some embodiments, the insulation on each of the electrical leads may sustain an electrical potential difference of between about 200 V to about 3,000 V across its thickness without dielectric breakdown. In some embodiments, the set of electrodes may include a plurality of electrodes. The plurality of electrodes may be grouped into one or more anode-cathode subsets such as, for example, a subset including one anode and one cathode, a subset including two anodes and two cathodes, a subset including two anodes and one cathode, a subset including one anode and two cathodes, a subset including three anodes and one cathode, a subset including three anodes and two cathodes, and/or the like.

The signal generator (222) may be configured to generate ablation pulse waveforms for irreversible electroporation of tissue, such as, for example, pulmonary vein ostia. For example, the signal generator (222) may be a voltage pulse waveform generator and deliver a pulse waveform to the ablation device (210).

In some embodiments, the signal generator (222) is configured to generate the ablation pulse waveform in synchronization with the indication of the pacing signal (e.g., within a common refractory window). For example, in some embodiments, the common refractory window may start substantially immediately following a ventricular pacing signal (or after a very small delay) and last for a duration of approximately 250 milliseconds (ms) or less thereafter. In such embodiments, an entire pulse waveform may be delivered within this duration.

The protection device (250) may be coupled between the cardiac stimulator (228) and the pacing device (230). As described in more detail herein, a control signal (also referred to herein as a protection signal) may be generated to synchronize operation of the protection device (250) with the generation of the pulse waveform by the signal generator (222). The protection device (250) may be configured to receive the control signal to control a state of the electrical connection between the pacing device (230) and the cardiac stimulator (228). For example, the protection device (250) may be configured to form an open circuit between the cardiac stimulator (228) and the pacing device (230) at least during delivery of ablation energy by the ablation device (210). Otherwise, the protection device (250) may be configured to electrically couple the pacing device (230) with the cardiac stimulator (228). In some embodiments, the protection device (250) may be configured to provide bi-directional open circuit isolation during high energy ablation energy delivery. In some embodiments, the protection device (250) may be formed separate from the cardiac stimulator (228) and/or the pacing device (230), and in other embodiments, the protection device (250) can be integrated into the cardiac stimulator (228) and/or pacing device (230). In some embodiments, the protection device (250) may include one or more of an internal power source (e.g., battery) and a power connector to couple to an external power source (e.g., medical grade power supply, wall-outlet). An internal power source may reduce ground noise injection.

In some embodiments, the cardiac stimulator (228), the protection device (250), and/or the signal generator (220) may be in communication with one another, e.g., for coordinating timing of the pulse waveform delivery, pacing signal delivery, and/or protection device control signal delivery. In some embodiments, the protection device (250), and/or the signal generator (220) may be in communication with one another, e.g., for coordinating timing of the pulse waveform delivery, pacing signal delivery, and/or protection device control signal delivery. In some embodiments, the protection device (250) may be integrated with the signal generator (222) in a single console.

In some embodiments, the cardiac stimulator (228), the protection device (250), and/or the signal generator (220) may be in communication with other devices (not shown) via, for example, one or more networks, each of which may be any type of network. A wireless network may refer to any type of digital network that is not connected by cables of any kind. However, a wireless network may connect to a wireline network in order to interface with the Internet, other carrier voice and data networks, business networks, and personal networks. A wireline network is typically carried over copper twisted pair, coaxial cable or fiber optic cables. There are many different types of wireline networks including, wide area networks (WAN), metropolitan area networks (MAN), local area networks (LAN), campus area networks (CAN), global area networks (GAN), like the Internet, and virtual private networks (VPN). Hereinafter, network refers to any combination of combined wireless, wireline, public and private data networks that are typically interconnected through the Internet, to provide a unified networking and information access solution. The system (100) may further comprise one or more output devices such as a display, audio device, touchscreen, combinations thereof, and the like.

The cardiac stimulator (228), the protection device (250), and/or the signal generator (220) can include one or more processor(s), which can be any suitable processing device configured to run and/or execute a set of instructions or code. The processor may be, for example, a general purpose processor, a Field Programmable Gate Array (FPGA), an Application Specific Integrated Circuit (ASIC), a Digital Signal Processor (DSP), and/or the like. The processor may be configured to run and/or execute application processes and/or other modules, processes and/or functions associated with the system and/or a network associated therewith (not shown). The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like.

The cardiac stimulator (228), the protection device (250), and/or the signal generator (220) can include one or more memory or storage device(s), which can be, for example, a random access memory (RAM), a memory buffer, a hard drive, an erasable programmable read-only memory (EPROM), an electrically erasable read-only memory (EEPROM), a read-only memory (ROM), Flash memory, etc. The memory may store instructions to cause the processor of any one of the cardiac stimulator (228), the protection device (250), and/or the signal generator (220) to execute modules, processes and/or functions, such as pulse waveform generation, isolation/protection, and/or cardiac pacing.

While FIG. 4 depicts a system including a separate cardiac stimulator (228), in some embodiments, cardiac stimulator (228) may form a part of and/or be integrated into signal generator (222). In some embodiments, one or more electrodes (212, 232, 234) may function as sensing electrodes.

Figure 5:
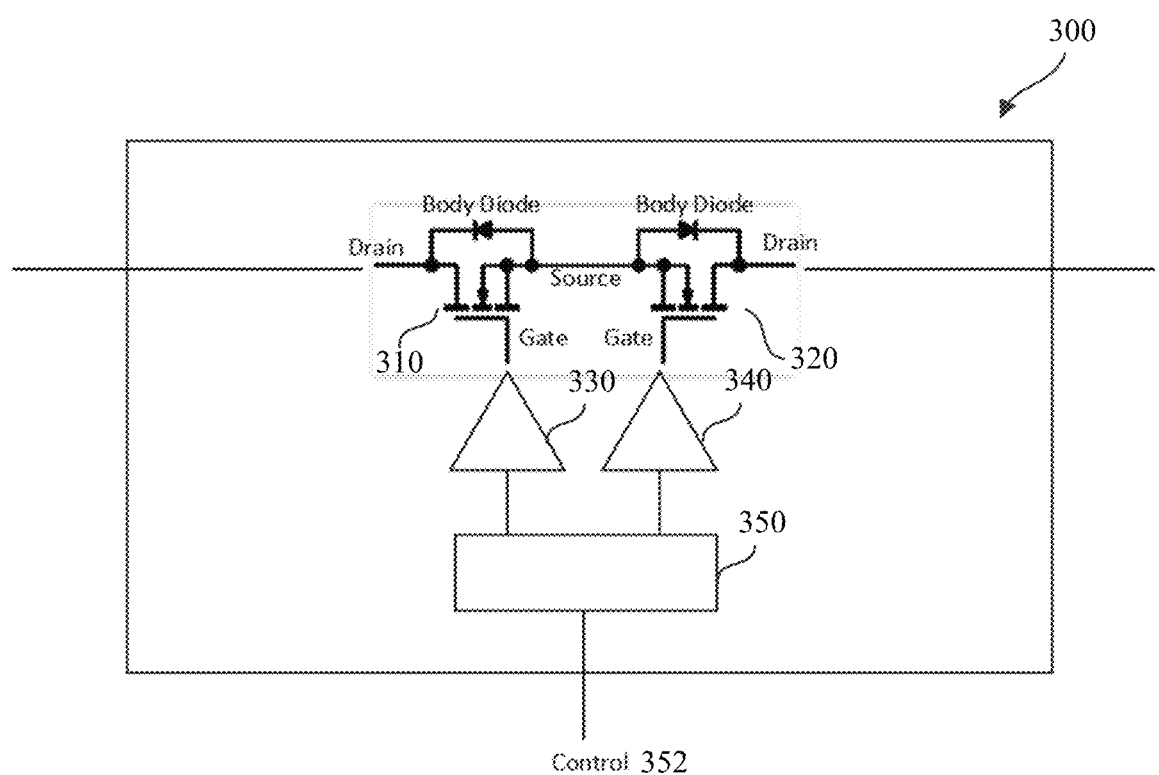
FIG. 5 is a circuit diagram of a protection device for protecting electronic components from high voltage signals, according to embodiments.

FIG. 5 is a circuit diagram of a protection device (300) including a first MOSFET (310) and a second MOSFET (320). The MOSFETs (310, 320) can be arranged as back-to-back MOSFETs with common source terminals such that the body diodes of the MOSFETs (310, 320) are in opposing directions. Such an arrangement can provide bi-directional isolation with precise timing control. The MOSFETs (310, 320) can be driven by isolated gate-drive circuits (330, 340). Specifically, the first MOSFET (310) can be coupled to a first gate driver (330), and the second MOSFET (320) can be coupled to a second gate driver (340). The first and second gate drivers (330, 340) may be coupled to a coupling (350) (e.g., an isolation/optical coupling) that can receive a control signal 352. The protection device (300) may be configured to reduce high voltage coupling of connected devices. For example, the protection device (300) may be configured to withstand voltages of up to about 3,000 V delivered by an ablation device. The protection device (300) may be configured to transition between a closed-circuit configuration and an open-circuit configuration based on a received protection signal (352) (e.g., control signal) such that the protection device (300) is in an open-circuit configuration for the duration of high-voltage ablation energy delivery and in a closed-circuit configuration at other times, e.g., to enable delivery of a pacing signal.

Methods

Also described here are methods for protecting electronic circuitry from induced currents and voltages during a tissue ablation process performed in one or more heart chamber(s) using the systems and devices described herein. In an embodiment, the heart chamber(s) may be the left atrial chamber and include its associated pulmonary veins. Generally, the methods described here include introducing and disposing a pacing device (e.g., pacing device (230)) in contact with one or more heart chamber(s). The pacing device may deliver a pacing signal to the heart using a cardiac stimulator (e.g., cardiac stimulator (228)) and/or measure cardiac activity. An ablation device (e.g., ablation device (210)) may be introduced and disposed in contact with one or more pulmonary vein ostial or antral regions. A pulse waveform may be delivered by one or more electrodes (e.g., electrodes (212)) of the ablation device to ablate tissue. In some embodiments, a protection device (e.g., protection device (250)) can be in an open-circuit configuration to isolate one or more sensitive electrical components (e.g., cardiac stimulator) during the delivery of the pulse waveform. Such electrical components may otherwise be electrically coupled to the pacing device and configured to deliver pacing signals to the heart and/or receive cardiac activity measurements. In some embodiments, a control signal may be generated to control the open-circuit interval (e.g., protection interval) of the protection device. The control signal may be based on one or more of a cardiac pacing signal, pulse waveform signal (e.g., signal generator signal), measured cardiac activity (e.g., R-wave detection), combinations thereof, and the like.

Additionally or alternatively, the pulse waveforms may include a plurality of levels of a hierarchy to reduce total energy delivery, e.g., as described in International Application Serial No. PCT/US2019/031135, filed on May 7, 2019, and titled "SYSTEMS, APPARATUSES AND METHODS FOR DELIVERY OF ABLATIVE ENERGY TO TISSUE," and incorporated herein by reference.

In some embodiments, the ablation devices (e.g., ablation device (210)) described herein may be used for epicardial and/or endocardial ablation. Examples of suitable ablation catheters are described in International Application Serial No. PCT/US2019/014226, incorporated by reference above.

Figure 6A:
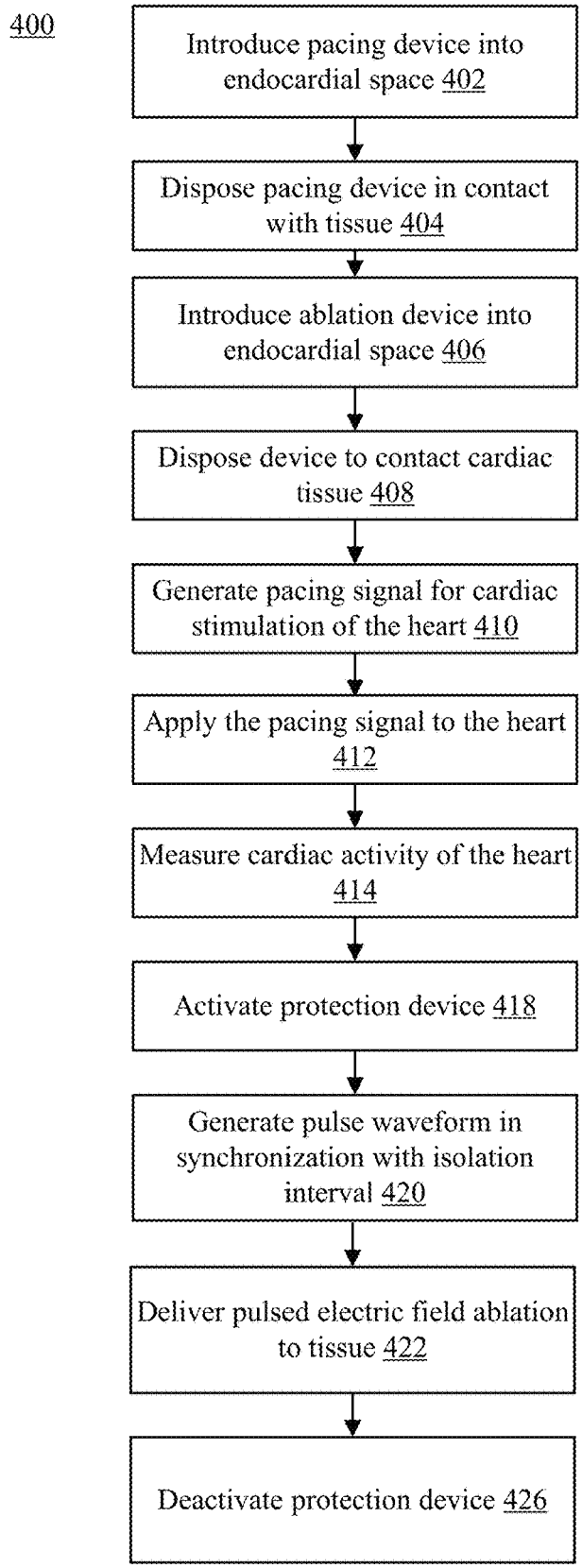
FIG. 6A illustrates a method for protecting electronic components from high voltage signals, according to embodiments.

FIG. 6A is an example method (400) of tissue ablation where ablation energy is delivered in synchrony with cardiac pacing. In some embodiments, the voltage pulse waveforms described herein may be applied during a refractory period of the cardiac cycle so as to avoid disruption of the sinus rhythm of the heart. The method (400) includes introduction of a pacing device (e.g., pacing device (230)) into an endocardial space, e.g., of a right ventricle, at (402). The pacing device may be advanced to be disposed in contact with the cardiac tissue, at (404). For example, sensor electrodes may be configured for cardiac activity measurement (e.g., ECG signals) and pacing electrodes may be configured for delivering pacing signals and may be disposed in contact with an inner endocardial surface, for example in the right ventricle. An ablation device (e.g., ablation device (210))

may be introduced into an endocardial space, e.g., of a left atrium, at (406). The ablation device may be advanced to be disposed in contact with a pulmonary vein ostium, at (408). In some embodiments, a pacing signal may be generated by a cardiac stimulator (e.g., cardiac stimulator (228)) for cardiac stimulation of the heart, at (410). The pacing signal may then be applied to the heart, at (412), using the pacing electrodes of the pacing device. For example, the heart may be electrically paced with the pacing signal to ensure pacing capture to establish periodicity and predictability of the cardiac cycle. One or more of atrial and ventricular pacing may be applied. Examples of applied pacing signals relative to patient cardiac activity are described in more detail herein, e.g. FIG. 7B.

In some embodiments, pacing capture may be automatically confirmed by one or more of a signal generator (e.g., signal generator (222)), the cardiac stimulator, or other processor operatively coupled to one or more components of the system. In some embodiments, pacing capture can be confirmed by a user. For example, the user may confirm pacing capture using a user interface (e.g., an input/output device such as a touch screen monitor or other type of monitor) based on measured cardiac activity signals. If the signal generator, processor, and/or the user viewing the displayed cardiac output, determines that there is an absence of pacing capture, pulse waveform generation may be prohibited and the user may be prompted to adjust system parameters by, for example, repositioning the pacing device to improve tissue engagement and/or modify pacing signal parameters (e.g., pulse width, pulse amplitude, pulse frequency, etc.).

In some embodiments, the pacing device may measure cardiac activity (e.g., ECG signals) corresponding to electrical cardiac activity of the heart, at (414). For example, the measured cardiac activity may include a measured cardiac pacing pulse, R-wave, etc.

A control signal or protection signal may be generated based on one or more of a cardiac pacing signal, pulse waveform signal (e.g., a signal received form a signal generator), measured cardiac activity (e.g., R-wave detection, predetermined voltage thresholds), combinations thereof, and the like, and applied to the protection device at (418). For example, the protection signal may be generated based on a cardiac pacing signal received from a cardiac stimulator (e.g., cardiac stimulator (128)) or a ECG signal measured by the pacing device (e.g., pacing device (230)). As another example, the protection signal may be generated based at least in part on a pulse waveform signal received from a signal generator (e.g., signal generator (222)). The protection signal may have a predetermined time period and length. The cardiac stimulator and/or other electronic components may be electrically isolated throughout a protection interval in response to the protection signal, at (418). For example, a protection device coupled to a pacing device may electrically isolate the cardiac stimulator from high voltage pulsed electric field ablation signals delivered by an ablation system (e.g., signal generator (222), ablation device (210), etc.) based on a received protection signal.

In some embodiments, a protection signal may synchronize electrical isolation of a cardiac stimulator with delivery of ablation energy to tissue. For example, the protection signal may be generated based on one or more of a cardiac pacing signal, measured cardiac activity, and signal generator signal, as described in detail herein. Additionally or alternatively, a protection device may generate a protection signal even when a cardiac stimulator is not actively delivering pacing signals during a pulsed electric field ablation procedure. This may be useful, for example, in case of a medical emergency requiring rapid cardiac pacing. Such protection can also be useful to isolate electronic components (e.g., medical electronic equipment other than the ablation device including, without limitation, ECG recording or monitoring equipment, electroanatomical mapping systems, device navigation/tracking systems, etc.) that are often present in a clinical procedure room. It is important to note that subsequent to delivery of a set of ablation pulses, the protection device is deactivated (424) so that connections are restored between the medical device electrode(s) and the respective electronic component(s) (e.g., medical electronic equipment, cardiac stimulator, electroanatomical mapping system, ECG recording or monitoring system, device navigation/tracking system, etc.).

The signal generator (e.g., signal generator (222) or any processor associated therewith may be configured to generate a pulse waveform in synchronization with the protection interval, at (420), e.g., based on predetermined criteria. For example, the pulse waveform may be generated during a refractory time period, which starts after and ends before the protection interval. The refractory time period may follow a pacing signal. For example, a common refractory time period may be between both atrial and ventricular refractory time windows. A voltage pulse waveform may be applied in the common refractory time period. In some embodiments, the pulse waveform and/or protection signal may be generated with a time offset with respect to the indication of the pacing signal. For example, the start of a refractory time period may be offset from the pacing signal by a time offset. The voltage pulse waveform(s) may be applied over a series of heartbeats over corresponding common refractory time periods. In some embodiments, the pulse waveform and protection signal may be generated based on the same or different signal or information (e.g., pacing signal, sensed R-wave).

The ablation device, in response to receiving the pulsed waveform, can generate an electric field that is delivered to tissue, at (422).

In some embodiments, hierarchical voltage pulse waveforms having a nested structure and a hierarchy of time intervals as described herein may be useful for irreversible electroporation, providing control and selectivity in different tissue types. For example, a pulse waveform may be generated by a signal generator (e.g., the signal generator (222)) and may include a plurality of levels in a hierarchy. A variety of hierarchical waveforms may be generated with a signal generator as disclosed herein. For example, the pulse waveform may include a first level of a hierarchy of the pulse waveform including a first set of pulses. Each pulse has a pulse time duration and a first time interval separating successive pulses. A second level of the hierarchy of the pulse waveform may include a plurality of first sets of pulses as a second set of pulses. A second time interval may separate successive first sets of pulses. The second time interval may be at least three times the duration of the first time interval. A third level of the hierarchy of the pulse waveform may include a plurality of second sets of pulses as a third set of pulses. A third time interval may separate successive second sets of pulses. The third time interval may be at least thirty times the duration of the second level time interval.

In some embodiments, the pulse waveform may be delivered to pulmonary vein ostium of a patient via a set of splines of an ablation device (e.g., ablation device (210)), or to a device positioned at any location in the cardiac anatomy or more generally in other parts of the patient anatomy. In some embodiments, voltage pulse waveforms as described herein may be selectively delivered to electrode subsets such as anode-cathode subsets for ablation and isolation of the pulmonary vein. For example, a first electrode of a group of electrodes may be configured as an anode and a second electrode of the group of electrodes may be configured as a cathode. These steps may be repeated for a desired number of pulmonary vein ostial or antral regions to have been ablated (e.g., 1, 2, 3, or 4 ostia). Suitable examples of ablation devices and methods are described in International Application No. PCT/US2019/014226, incorporated above by reference.

Figure 6B:
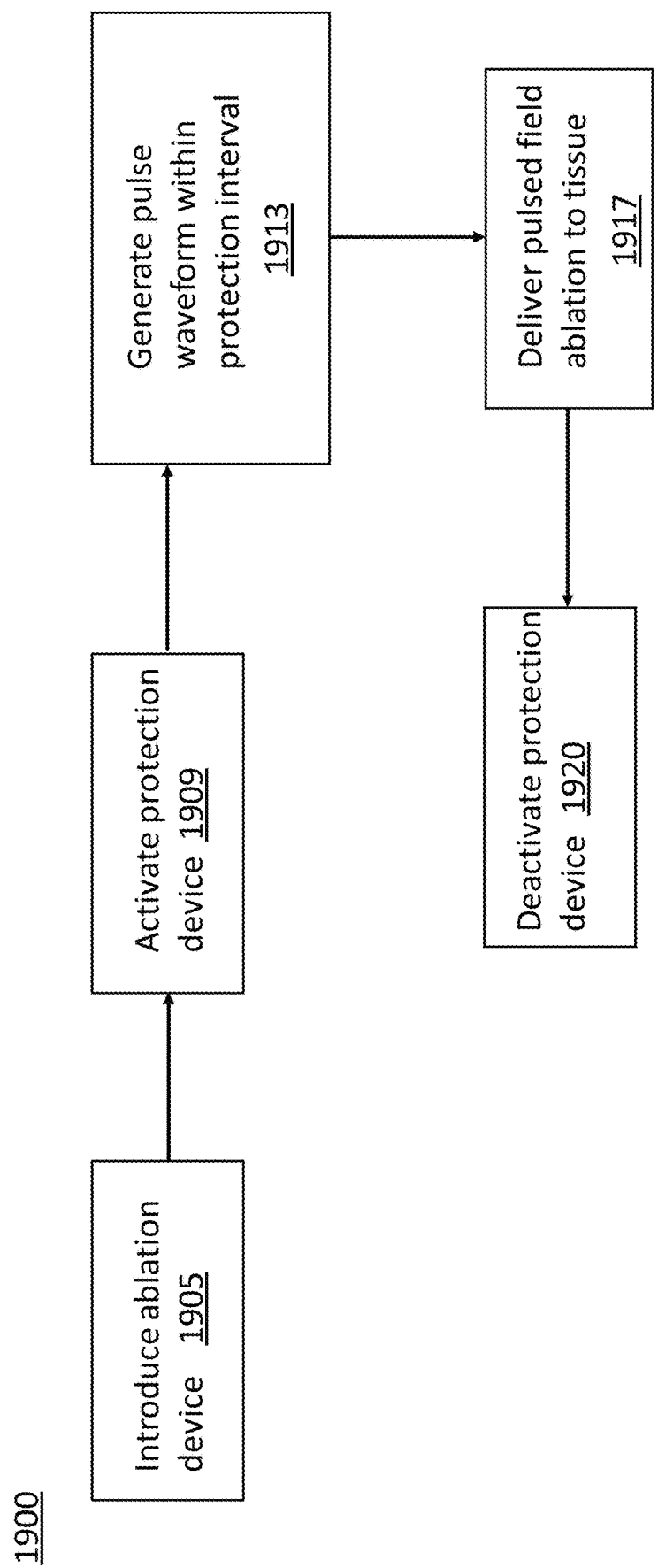
FIG. 6B illustrates a method for protecting electronic components from high voltage signals for asynchronous delivery of ablation, according to embodiments.

FIG. 6B is an example method (1900) of tissue ablation where ablation energy is delivered asynchronously (with no cardiac pacing). The ablation device is introduced in the patient anatomy and positioned in a region of interest, for example at a location in the cardiac anatomy where it is desired to ablate, at (1905). The protection device may be activated at (1909), e.g., by a suitable control signal that may be coupled directly to hardware switched isolation circuitry or to a processor that controls switched isolation circuitry. As used herein, a control element may refer to one or more of a control signal, processor, and a switch circuit (e.g., switched isolation circuitry). Thus, the electronic components or equipment to be protected are isolated from possible pickup of ablation pulses over an isolation time interval. A pulse waveform is generated at (1913) and delivered to tissue at (1917) within the isolation time interval. Subsequent to delivery of the ablation pulses at (1917), the protection device is deactivated at (1920) so as to restore electrical connectivity between the electronic component(s) or equipment and any relevant patient-contact electrodes. Such protected electronic equipment can include one or more cardiac stimulators, electroanatomical mapping systems, ECG recording/monitoring systems, device navigation/tracking systems, etc.

Figure 7A:
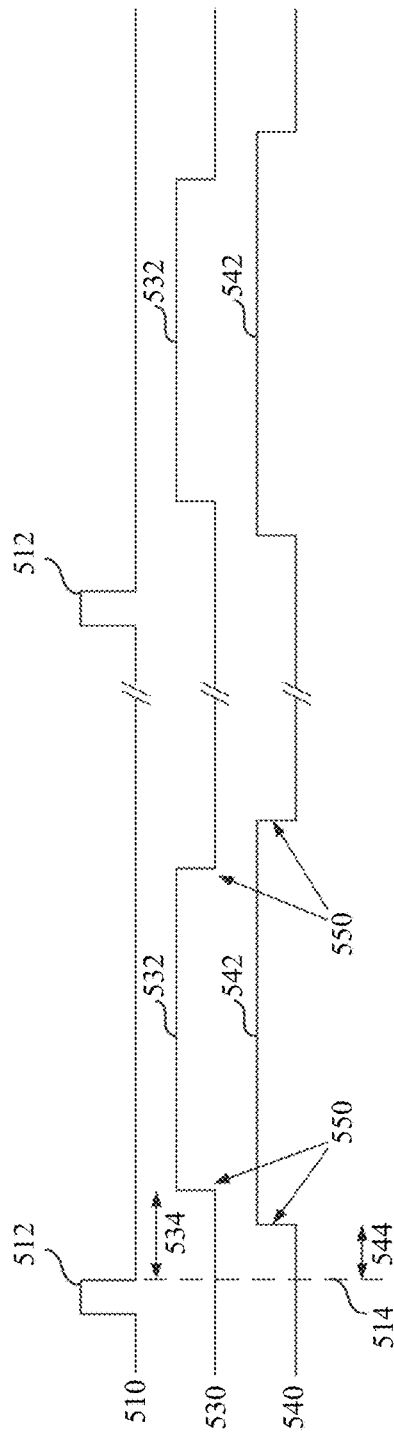
FIG. 7A illustrates a time sequence of a cardiac pacing signal, energy delivery, and device isolation, according to embodiments.
Figure 7B:
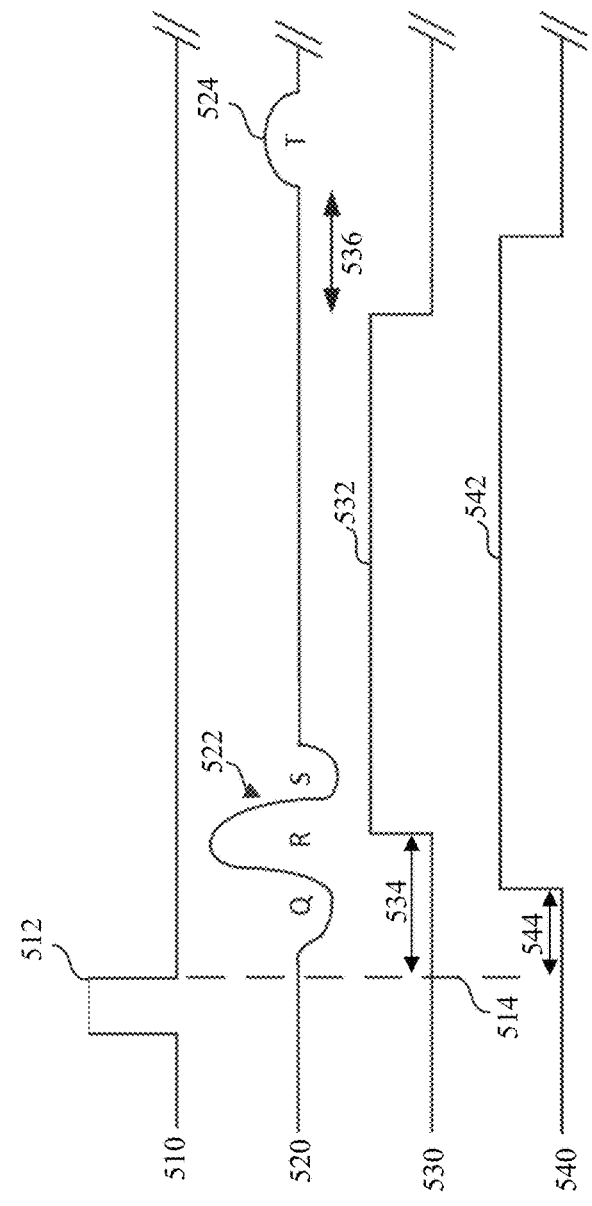
FIG. 7B illustrates a time sequence of a cardiac pacing signal, cardiac activity, energy delivery, and device isolation, according to embodiments.

For example, in embodiments where a cardiac stimulator is used to pace a heart over portions of a pulsed electric field ablation procedure, a patient connection between the cardiac stimulator and the heart needs to remain intact for the duration of a pacing or stimulation pulse. In such embodiments, a protection signal (e.g., control signal for activating a protection device) can synchronize electrical isolation of a cardiac stimulator with delivery of ablation energy to tissue. FIG. 7A is a schematic illustration of a time sequence of cardiac stimulation (510), pulsed electric field ablation delivery (530), and protection interval (540) (e.g., blanking or open-circuit) channels. FIG. 7B is a schematic illustration of a time sequence of cardiac stimulation (510), electrocardiogram (520), pulsed electric field ablation delivery (530), and protection interval (540) channels. The cardiac stimulation (510) may comprise a set of periodic pacing pulses (512). Each pacing pulse (512) may comprise a rectangular pulse having a width of between about 0.1 ms and about 20 ms. The pacing pulses (512) may be generated by a stimulator (e.g., stimulator (228)) and delivered to cardiac tissue using a pacing device (e.g., pacing device (230)). The pacing pulses (512) may correspond to one or more of ventricular and atrial cardiac pacing. In response to the pacing pulses (512), the cardiac cycle of the heart may synchronize with the pacing pulses (512). For example, the QRS waveform (522) in FIG. 7B is synchronized with a respective pacing pulse (512). The T-wave (524) that follows the QRS waveform (522) corresponds to the start of repolarization occurring in the cardiac myocytes. In some embodiments, electrocardiogram (520) may be measured using a pacing device.

In some embodiments, high-voltage application of a pulsed electric field ablation procedure can be synchronized with the cardiac cycle, as depicted in FIGS. 7A and 7B. Pacing can be synchronized to the high-voltage application in several ways. For example, atrial pacing, ventricular pacing, or multi-chamber pacing can be performed. It can be desirable to implement ventricular pacing as the ventricle is more prone to cause arrhythmias (e.g., ventricular tachycardia, ventricular fibrillation) if stimulated during its re-polarization (e.g., T-wave) period. When a stimulation pulse is applied, the high-voltage output of the pulsed electric field ablation can occur concurrent with the pacing or being a predetermined delay after the stimulation pulse.

In some embodiments, delivery of a pulse waveform (532) may begin a first delay (534) (e.g., time interval or period) after the trailing edge (514) of each pacing pulse (512). Each pulse waveform (532) can be applied during an interval (532). In some embodiments, the first delay (534) may be a predetermined value (e.g., input by a user). For example, the first delay (534) may be between about 1 ms and about 100 ms. A second pulse delay (536) can separate the end of the pulse waveform (532) delivery and the start of the T-wave. As described above, it can be desirable to deliver a pulse waveform during a refractory period associated with a cardiac cycle. Accordingly, this second pulse delay (536) represents a safety margin between the pulse waveform (532) and the T-wave (524).

A blanking interval or protection interval (542) can be configured to start immediately or shortly after each pacing pulse (512). The protection interval (542) can be configured to encapsulate the duration during which the pulse waveform (532) is delivered. For example, the protection interval (542) can begin a third delay (544) after the trailing edge (514) of the pacing pulse (512), where the third delay (544) is less than the first delay (534) of the pulse waveform (532). For example, the third delay (544) may be less than about 5 ms. The third delay (544) can be near zero but non-zero such that the protection interval (542) (e.g., open-circuit state, blanking interval) does not overlap the pacing pulse (512) since a closed-circuit connection is necessary for a stimulator and pacing device to deliver the pacing pulse (512). In some embodiments, the protection interval (542) is at least equal to and preferably greater than a first length of the pulse waveform (532) such that the protection interval (542) at least overlaps (e.g., encapsulates) the entire pulse waveform (532). In FIGS. 7A and 7B, the leading and trailing edges (550) of the pulse waveform (532) and protection interval (542) are such that the protection interval (542) is longer than the pulse waveform (532).

If the timing of the high-voltage application of the pulsed electric field ablation is known (e.g., with respect to the pacing or stimulation pulses of the cardiac stimulator), the protection interval (542) can be tailored around the duration of the high-voltage application to ensure that isolation protection encapsulates the high-voltage application interval. The signal generator for the high-voltage application can be configured to have a predetermined amount of delay (e.g., first delay (534)) between the stimulation pulse (e.g., pacing pulse (512)) and the initiation of the high-voltage application to the patient (e.g., leading edge (550) of pulse waveform (532)). This delay can provide sufficient time for the protection element to transition to its isolation state (e.g., open circuit state or configuration) and start the protection interval (542). The protection interval (542) then remains for a duration longer than the high-voltage application interval. The timing of the protection interval (542) and the pulse waveform (532) can be repeated for each cardiac cycle.

Figure 8:
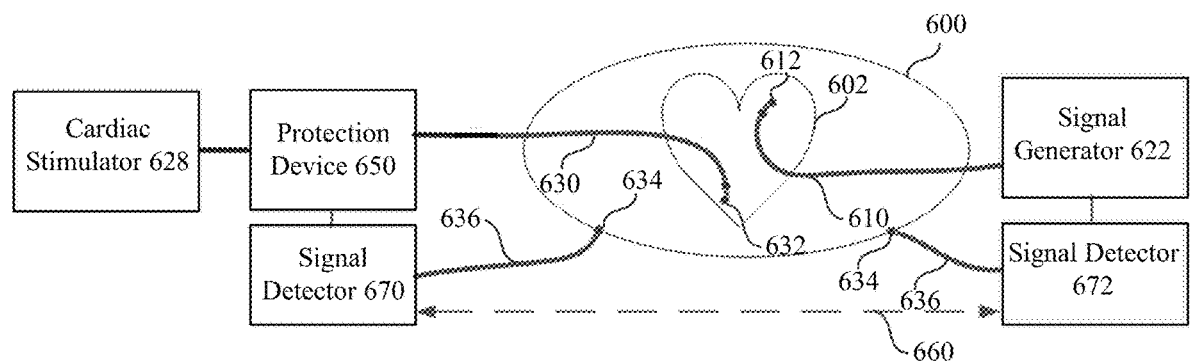
FIG. 8 is a schematic diagram of a system for protecting electrical components from high voltage signals, according to embodiments.

In some embodiments, cardiac sensing or monitoring e.g., for an R-wave (e.g., ventricular depolarization/contraction) can be used to synchronize delivery of ablation energy to tissue to the cardiac cycle. For example, the intrinsic R-wave of patient can be sensed and used as a trigger to one or more of ablation energy delivery and electrical isolation. In some embodiments, this R-wave sensing can be used in lieu of pacing the heart. In alternative embodiments, the R-wave sensing can be used along with pacing. For example, pacing can be performed in either the atria or ventricles, and the R-wave response of the captured beat can be sensed and used for synchronization. FIG. 8 is a schematic diagram of an electroporation system disposed in a heart (602) of a patient (600). The electroporation system may include an ablation device (610), signal generator (622) (e.g., pulsed field ablation generator), cardiac stimulator (628), pacing device (630), protection device (650), and one or more signal detectors (670, 672). While two signal detectors (670, 672) are depicted in FIG. 8, it can be appreciated that a single signal detector rather than two independent detectors can be used to accomplish the methods described herein.

The signal generator (622) may be coupled to the ablation device (610) and the signal detector (672). The signal generator (622) may be configured to generate pulse waveforms delivered to electrodes (612) of the ablation device (610), e.g., for delivering ablation energy to the heart (602). The pacing device (630) may be configured to pace the heart using pacing electrodes (632) of pacing device (630). One or more diagnostic devices (636) may be configured to measure cardiac activity of the heart (600) (e.g., electrocardiogram), e.g., using externally placed electrode pads or intra-cardiac electrodes (634). Alternatively, in some embodiments, one or more electrodes of the pacing device (630) and/or ablation device (610) can be used as sensing electrodes, which can connect to a processor (e.g., signal detector (670, 672)) for further detection and/or analysis of components of the cardiac cycle.

The protection device (650) may be coupled between the cardiac stimulator (628) and the pacing device (630). In some embodiments, the protection device (650) may be configured to synchronize electrical isolation of the cardiac stimulator (628) with delivery of ablation energy by the ablation device (610). The one or more signal detectors (670, 672) may be coupled to one or more of the signal generator (622), pacing device (630), protection device (650), and cardiac stimulator (628). As shown in FIG. 8, a first signal detector (670) is coupled to the protection device (650) and a second signal detector (672) is coupled to the signal generator (622). In alternative embodiments, however, a single signal detector can be coupled to both the protection device (650) and the signal generator (622).

Each signal detector (670, 672) may be coupled to a respective diagnostic device (636) coupled to the patient (600). Alternatively, the signal detectors (670, 672) may be integrated with one or more of the signal generator (622), pacing device (630), protection device (650), and cardiac stimulator (628). The signal analyzer (670) may be configured to receive and analyze an electrocardiogram signal to detect one or more R-waves. In some embodiments, R-waves may be detected using an R-wave amplitude threshold, together with some exclusion criteria for noise. When an R-wave is detected, the signal detector (670, 672) can be configured to output a signal to the protection device (650) and signal generator (622). Specifically, the signal detector (672) coupled to the signal generator (622), upon detecting an R-wave, can send a signal to the signal generator (622) to indicate the timing of the R-wave and therefore inform the signal generator (622) as to when to deliver the pulsed electric field ablation. The signal detector (670) coupled to the protection device (650), upon detecting an R-wave, can send a signal to the protection device (650) (e.g., a control signal as described above) to indicate the timing of the R-wave and therefore inform protection device (650) of when to initiate the protection or blanking interval, as further described with reference to FIG. 9.

Figure 9:
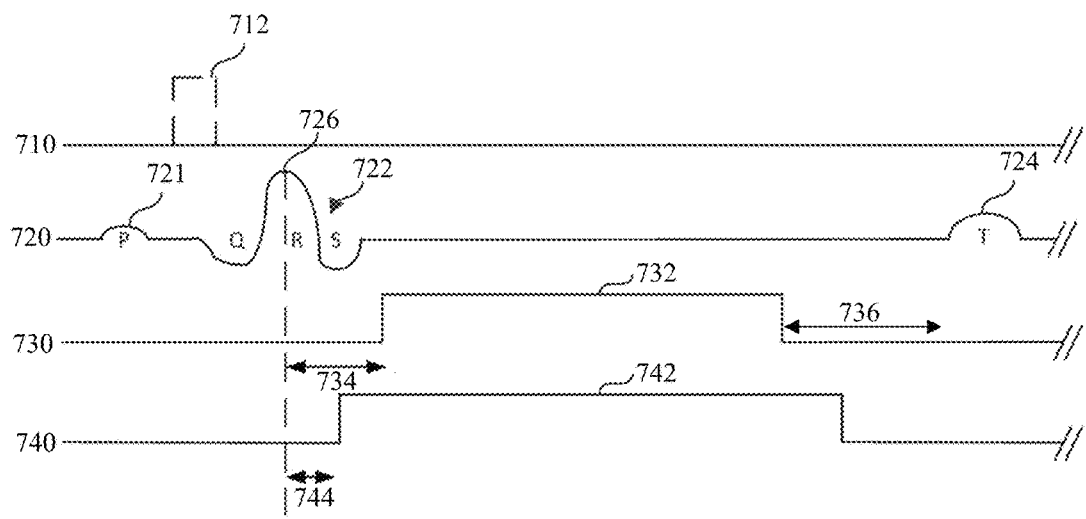
FIG. 9 illustrates a time sequence of a cardiac pacing signal, cardiac activity, energy delivery, and device isolation, according to embodiments.

FIG. 9 is a schematic illustration of a time sequence of cardiac stimulation (710), electrocardiogram (720), pulsed field ablation delivery (730), and protection interval (740) channels. The time sequence depicted in FIG. 9 can include aspects similar to the time sequence depicted in FIG. 7B. The cardiac stimulation (710), e.g., by a cardiac stimulator (628) as depicted in FIG. 8, can provide optional and/or periodic stimulation pulses (712) to a patient (e.g., patient (600)). In an embodiment, the stimulation pulses may be periodic and may comprise a rectangular pulse having a width of between about 1 ms and about 5 ms. In some embodiments, the pacing pulses (712) may be delivered using any of the pacing devices (e.g., pacing device (630)) described herein. The pacing pulses (712) may correspond to one or more of ventricular and atrial cardiac pacing. The electrocardiogram (720) can include one or more P-waves (721), QRS waveforms (722), and T-waves (724). The P-wave (721) corresponds to atrial depolarization. The T-wave (724) that follows the QRS waveform (722) corresponds to the start of repolarization occurring in the cardiac myocytes. In some embodiments, delivery of a pulse waveform (732) may be synchronized with R-wave (726) detection, e.g., immediately upon R-wave detection or after a first delay (734). In embodiments where a protection device (e.g., protection device (650)) is used to isolate certain electronic components from the patient during pulsed electric field ablation delivery, it can be desirable to implement a predetermined delay such that there is sufficient time for the protection device to isolate such electronic components after R-wave detection and before pulsed electric field ablation delivery. In some embodiments, the first delay (734) may be a predetermined value. For example, the first delay (734) may be between about 1 ms and about 5 ms. In some embodiments, the pulse waveform (732) may be separated from a T-wave (724) by a second delay (736), e.g., to provide a safety margin.

In some embodiments, a protection device (e.g., protection device (650)) that implements a protection interval (742) (e.g., open-circuit or blanking interval) can use R-wave (726) detection for synchronization. The protection device can start the protection interval (742) after a third delay (744) from the R-wave (726). The third delay (744) may be less than the first delay (734). The third delay (744) may be less than about 5 ms. When a protection device is used with cardiac stimulation, the protection interval (742) (e.g., open-circuit state, blanking interval) can be configured to not overlap the stimulation or pacing pulse (712). The protection interval (742) may be at least equal to, and preferably greater than, a length of the pulse waveform (732) such that the protection interval (742) at least overlaps (e.g., encapsulates) the entire pulse waveform (732). In some embodiments, the pulse waveform (732) and the protection interval (742) can be implemented independently (e.g., with separate R-wave detectors (670, 672)) or concurrently (e.g., with a single R-wave detector (670)). By starting the protection interval (742) immediately or shortly after R-wave (726) detection and having it continue for longer than the expected pulsed field ablation delivery duration, the protection interval (742) can protect electronic components (e.g., sensitive equipment such as, for example, the cardiac stimulator) even when intra-cardiac pacing is not actively being used during a pulsed field ablation procedure. It can be important to protect such electronic components such as a cardiac stimulator, even if such equipment is not actively being used during an ablation procedure, in the event of medical emergencies that may require rapid pacing or other types of pacing and therefore permitting such electronic components to be functional, connected, and ready to use throughout the procedure.

Figures 10A, 10B, 10C, 10D, 10E:
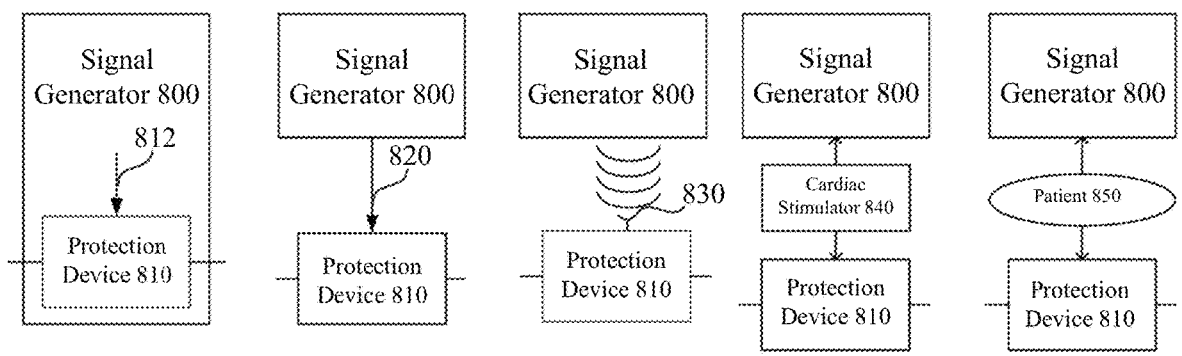
FIGS. 10A-10E are block diagrams of alternative arrangements of a protection device and a high voltage generator, according to embodiments.

The protection devices described herein can be a separate piece of equipment or can be integrated into ancillary equipment or a pulsed field ablation stimulator. FIGS. 10A-10E are block diagrams of a set of systems including protection devices, both integrated with and separate from other system components. FIG. 10A illustrates a signal generator (800) (e.g., for pulsed electric field ablation) comprising a protection device (810) integrated therewith. For example, one or more of the signal generator (800), protection device (810), cardiac stimulator (e.g., cardiac stimulator (228)), and signal analyzer (e.g., signal detector (670)) may be integrated into a single enclosure (e.g., housing, signal generator console). This may allow sensitive electronic circuitry to be protected within the same enclosure from high voltage noise. External electrical components (e.g., ancillary equipment) may be similarly protected by coupling such components to the protection device (810) at a point further downstream from the high voltage exposure point (e.g., the patient). For example, external equipment can be protected by routing signals received by the system through the protection device (810) before having those signals reach the patient, such that the protection device (810) can time its blanking interval to coincide with times of potential high voltage exposure. With the integrated configuration depicted in FIG. 10A, a digital "blanking" signal (e.g., control signal) can be provided to the protection device by the signal generator (800) to indicate the necessary time for isolation (e.g., protection) of sensitive electronic components. The "blanking" signal may be configured to control the protection device to electrically isolate a set of electronic components internal and external to the signal generator (800), thereby providing coordinated and robust protection.

In some embodiments, manually operated switches can be configured to be a protection device to protect electronic components or equipment from ablation-induced noise.

In some embodiments, the signal generator and protection device may be separate pieces of equipment (e.g., formed in different enclosures). In such embodiments, control signals can be transmitted between the signal generator and protection device via wired or wireless communications; however, wired control signals can be more robust and avoid the risk of delay more often associated with wireless communications. With an external or separate protection device, the protection device can be either battery-powered or wall-powered, e.g., using medical grade isolation, but battery-powered protection devices can be more desirable to reduce ground noise injection into the patient from isolated wall power supplies. FIG. 10B illustrates a signal generator (800) coupled to a protection device (810) via a wired connection (820) (e.g., power/data cable). FIG. 10C illustrates a signal generator (800) coupled to a protection device (810) via a wireless connection. For example, the protection device (810) may comprise a wireless transceiver (830) configured to receive a control signal (e.g., transmitted from the signal generator (800)).

In embodiments where the protection device is implemented independently from the signal generator (e.g., pulsed field ablation generator), the protection device requires a mechanism for synchronizing with delivery of high voltages pulses such that it can effectively isolate certain electronic components during such delivery. In some embodiments, a protection signal may synchronize electrical isolation of certain electronic components (e.g., a stimulator) with delivery of ablation energy to tissue based on one or more of a timed-trigger pulse from a stimulator, stimulation-pulse sensing (e.g., of stimulation pulses for cardiac capture), measured cardiac activity (e.g., R-wave detection, and/or high-voltage sensing (e.g., with rapid application of isolation upon detection of a high voltage spike on a patient side). Such is further described below with reference to FIG. 12. FIGS. 10D and 10E illustrate two configurations of implementing synchronization. Such configurations are similar to those described with respect to FIGS. 7A-9. FIG. 10D illustrates a signal generator (800) and a protection device (810), both configured to receive signals from a cardiac stimulator (840). The cardiac stimulator (840) may be configured to synchronize ablation energy delivery by the signal generator (800) and electrical isolation by the protection device (810) through output of respective signals (e.g., a trigger or control signal) to the signal generator (800) and the protection device (810). FIG. 10E illustrates a signal generator (800) and a protection device (810) both coupled to a patient (850) and configured to operate in synchronicity with one another based on measured data (e.g., cardiac stimulation or pacing pulse, R-wave detection, high voltage detection). When implementing synchronization based on stimulation pulse detection, a sufficiently high predetermined threshold (e.g. 5 V) can be set to reduce the likelihood of false-positive sensing, which can undesirably lead to increased occurrences of isolation and disconnection of protected electrical components from a patient.

Figure 11:
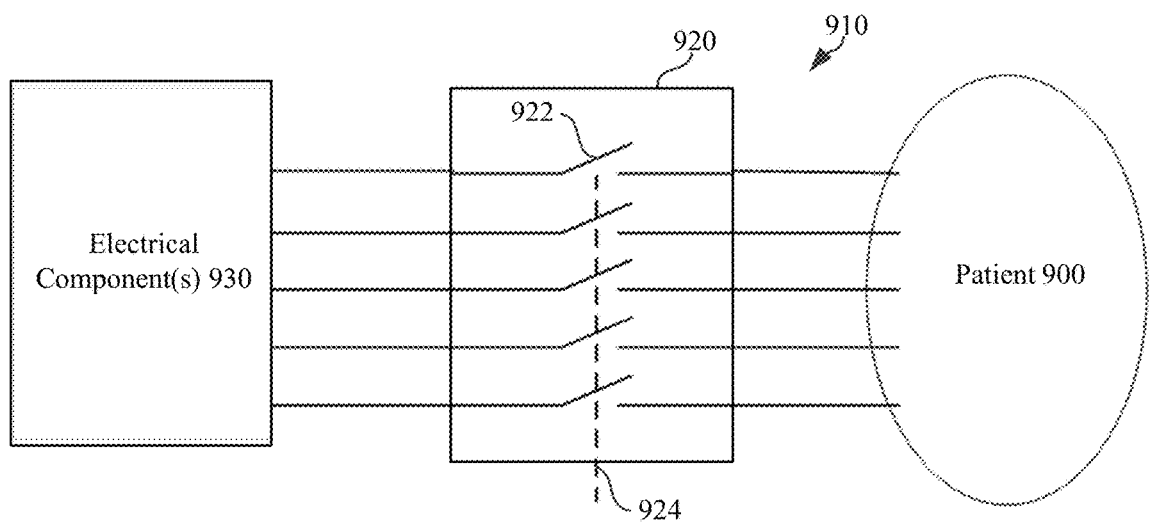
FIG. 11 is a schematic diagram of a protection device for controlling connections between electronic components operating in a high voltage exposure area, according to embodiments.

Protection devices as described herein can be configured to isolate a plurality of electrical components (e.g., sensitive circuitry or equipment) from high voltages and induced currents. FIG. 11 is a block diagram of a system (910) coupled to a patient (900). One or more devices of the system (910) (e.g., pacing device, catheters, stylets, probes, electrodes, etc.) may be coupled to the patient (900) and may be susceptible to induced current from high voltage ablation energy delivery. Each of the devices of the system (910) may be coupled to a protection device (920) configured to selectively electrically isolate electrical components disposed downstream from the protection device (920) from those portions of devices disposed in the heart and are exposed to the high voltages. In some embodiments, a single protection signal (924) may be configured to control the protection device (920) and provide electrical isolation, e.g., through a plurality of switches (922), of the plurality of electronic component(s) simultaneously.

Figure 12:
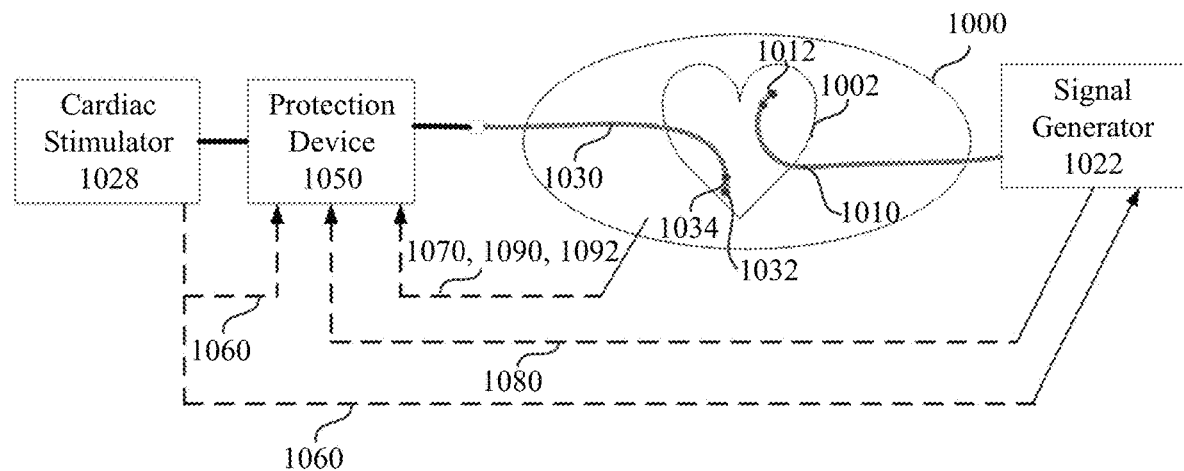
FIG. 12 is a schematic diagram of a system for protecting electronic components from high voltage signals, according to embodiments.

As noted, in some embodiments, e.g., where a protection device is implemented as an independent system without signals being communicated from a high voltage pulse generator (e.g., for pulsed field ablation), the operation of the protection device can be synchronized based on stimulation-pulse sensing, trigger pulses from a cardiac stimulator, R-wave sensing, or high-voltage sensing. FIG. 12 is a schematic diagram of an electroporation system disposed in a heart (1002) of a patient (1000) that includes an ablation device (1010), signal generator (1022), cardiac stimulator (1028), pacing device (1030), and protection device (1050). The signal generator (1022) may be coupled to the ablation device (1010). The signal generator (1022) may be configured to generate pulse waveforms delivered to electrodes (1012) of the ablation device (1010) for generating a pulsed electric field for ablation. The pacing device (1030) may be configured to pace the heart (1002) using pacing electrodes (1032, 1034) and/or measure cardiac activity of the heart (1002) (e.g., electrocardiogram) using one or more electrodes (e.g., electrodes (1032, 1034) or other electrodes (not depicted)). The protection device (1050) may be coupled between the cardiac stimulator (1028) and the pacing device (1030).

In some embodiments, the protection device (1050) may be configured to synchronize electrical isolation of the cardiac stimulator (1028) with pulse waveform delivery by the ablation device (1010) based on one or more signals. The protection device (1050) may be synchronized based on the same signal or combination of signals as the signal generator (1022) or independently based on one or more of a stimulation signal (1060) from the cardiac stimulator (1028) (which can also be sent to the signal generator (1022)), measured data (e.g., stimulation-pulse detection signal (1070), R-wave detection signal (1090), and high-voltage detection signal (1092)), and a signal generator signal (1080). In alternative embodiments, the protection device (1050) and the signal generator (1022) can be activated based on different signals or a different combination of signals. For instance, the protection device (1050) may be controlled based on a cardiac pacing signal (1060) and pulse waveform delivery may be based on a detected R-wave signal (1090). In embodiments using stimulation pulse sensing, the sensing can be implemented with a predetermined threshold (e.g., about 5V) in order to reduce false-positives that may increase the number of disconnections between the cardiac stimulator (1028) and/or other protected electronic components and the patient (1000).

Figure 13:
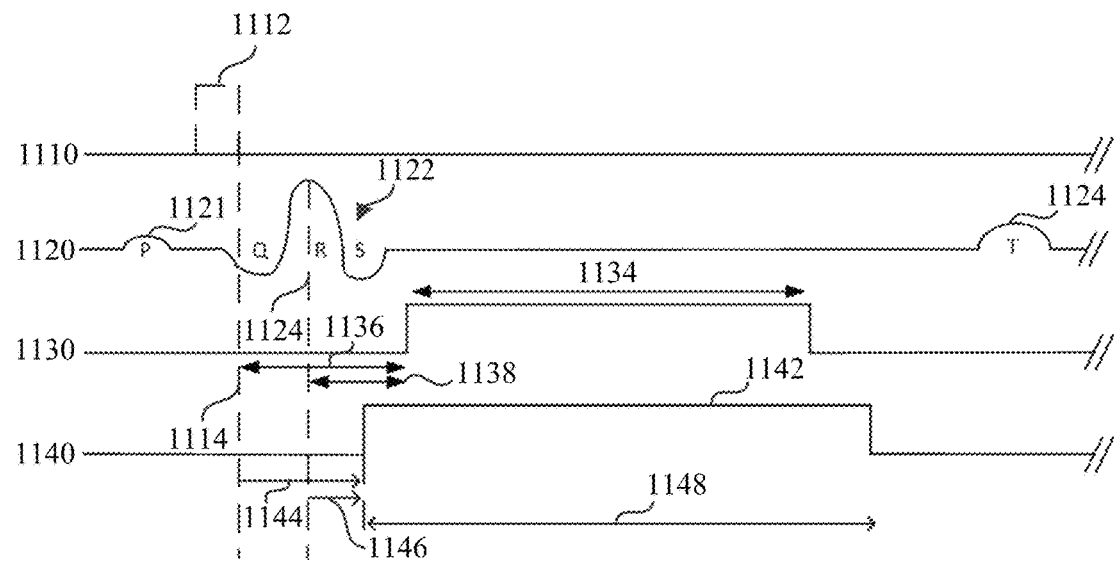
FIG. 13 illustrates a time sequence of a cardiac pacing signal, cardiac activity, energy delivery, and device isolation, according to embodiments.

Protection or isolation coverage of certain electronic components during a high voltage interval can be implemented using a fixed blanking interval sufficiently long in duration to cover a longest expected ablation interval or an adjustable or settable blanking interval (e.g., which a user or system can set to a value based on expected pulsed field ablation time). FIG. 13 is a schematic illustration of a time sequence of a cardiac stimulation (1110), electrocardiogram (1120), pulsed field ablation delivery (1130), and protection interval (1140) channels. The cardiac stimulation (1110) channel can optionally include pacing or stimulation signals (1112) that may be periodic and may comprise a rectangular pulse having a width of between about 0.1 ms and about 100 ms. In some embodiments, the pacing pulses (1112) may be delivered using any of the pacing devices (e.g., pacing devices (230, 630, 1030)) described herein. The pacing pulses (1112) may correspond to one or more of ventricular and atrial cardiac pacing. In response to the pacing pulses (1112), the cardiac cycle of the heart may synchronize with the pacing pulses (1112). For example, the P-wave (1121), QRS waveform (1122), and T-wave (1124) in FIG. 13 can be synchronized with the pacing pulse (1112). The P-wave (1121) corresponds to atrial depolarization, and the T-wave (1124) that follows the QRS waveform (1122) corresponds to the start of repolarization occurring in the cardiac myocytes.

In some embodiments, a pulse waveform (1132) and protection interval (1142) may synchronize based on one or more of pacing or stimulation pulse sensing (1144) and R-wave detection (1124). The pulse waveform (1132) may have a first length or duration (1134), and the protection interval (1142) may have a second length or duration (1148) at least as long as the duration of the pulse waveform (1132). The duration (1148) of the protection interval (1142) can be fixed or adjustable. The pulse waveform (1134) may be delivered after a first delay (1136) from a trailing edge (1114) of the cardiac pacing pulse (1112) (e.g., as signaled by a cardiac stimulator or detected). The first delay (1136) may be a predetermined value. For example, the first delay (1136) may be between about 1 ms and about 5 ms. Likewise, a protection interval (1142) may synchronize with the cardiac pacing pulse (1112) (e.g., as signaled by a cardiac stimulator or detected) after a second delay (1144). In this manner, a cardiac pacing signal (1112) may be configured to trigger the protection interval (1142). The protection interval (1142) (e.g., open-circuit state, blanking interval) can overlap the entire pulse waveform (1132).

In some embodiments, the pulse waveform (1132) and protection interval (1142) may synchronize with R-wave detection (1124), e.g., after respective third delay (1138) and fourth delay (1146). In this manner, the R-wave detection (1124) may be configured to trigger the protection interval (1142). The R-wave detection can be implemented using any of the systems as described herein. The third delay (1138) may be a predetermined value. For example, the third delay (1138) may be between about 1 ms and about 20 ms. In some embodiments, the pulse waveform (1132) and the protection interval (1142) may begin substantially concurrently with the R-wave detection (1124).

In some embodiments, one or both of the second delay (1144) and the fourth delay (1146) can be adjustable such that the protection interval (1142) can have a duration (1148) that is adjustable.

Figure 14:
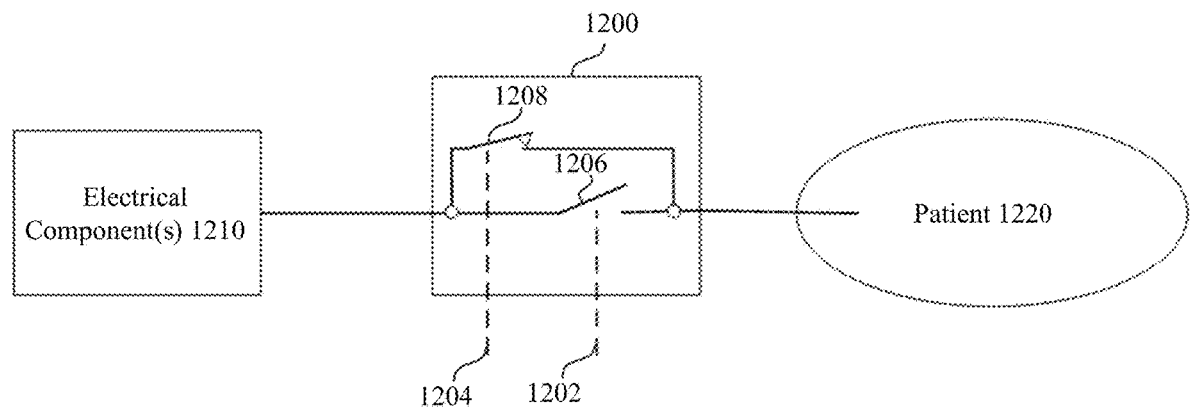
FIG. 14 is a schematic diagram of a protection device for controlling connections between electronic components operating in a high voltage exposure area, according to embodiments.

To provide another layer of safety, a protection device for any external electronic components can be configured to provide a low-impedance connection between the protected electronic components and the patient when unpowered. FIG. 14 is a block diagram of electrical component(s) (1210) (e.g., including sensitive equipment or circuitry) coupled to a patient (1220) via a protection device (1200). One or more electrical component(s) (1210) (e.g., cardiac stimulator, such as any described herein) may be coupled to the patient (1220) and may be susceptible to induced current from high voltage ablation energy delivery. Each of the electrical component(s) (1210) may be coupled to the protection device (1200) to selectively electrically isolate those components from devices disposed in the heart of the patient (1220). The protection device (1200) can be configured such that the electrical component(s) (1210) are electrically coupled (e.g., through a low-impedance connection) to the patient (1220) when the protection device (1200) is unpowered. This safety feature may allow for patient connection by default and allow the electrical component(s) (1210) to operate even if power is lost to the protection device (1200). For example, a cardiac stimulator (e.g., cardiac stimulator (128)) included in the electrical component(s) (1210) may provide pacing to the patient (1220) when the protection device (1200) is powered off.

A first signal (1202) (e.g., control signal) may be configured to control the protection device (1200) and provide electrical isolation through a first switch (1206) as described herein. A second signal (1204) (e.g., a power signal) may be configured to control the protection device (1200) through a second switch (1208). In some embodiments, the second switch (1208) may comprise a relay (e.g., reed switch, or solid-state type switch) configured in parallel to the first switch (1206) used for isolation/blanking and configured to switch open when the protection device (1200) is powered. This second pathway provided via the second switch (1208) can normally be set to a closed state to provide the low-impedance connection between the electrical component(s) (1210) and the patient (1220).

Figure 15:
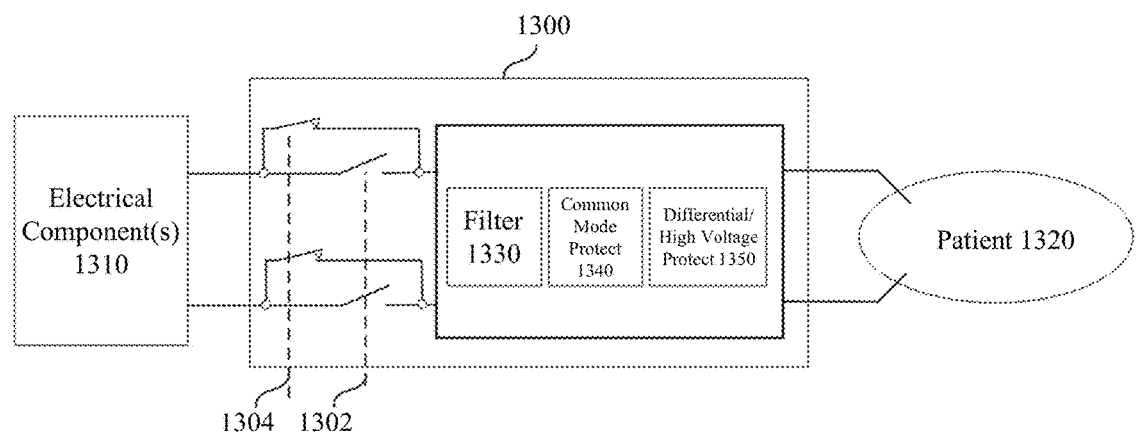
FIG. 15 is a schematic diagram of a protection device for controlling connections between electronic components operating in a high voltage exposure area, according to embodiments.

FIG. 15 provides another example embodiment for a system including a protection device (1300). Specifically, FIG. 15 is a block diagram of electrical component(s) (1310) coupled to a patient (1320) via a protection device (1300). One or more electrical component(s) (1310) (e.g., cardiac stimulator) may be coupled to the patient (1320) via the protection device (1300) configured to selectively electrically isolate those electrical components) (1310) from devices disposed in the heart of the patient (1320), e.g., via a first signal (1302). In a similar manner as described with respect to FIG. 14, the electrical component(s) (1310) may be electrically coupled to the patient (1320) when the protection device (1300) is unpowered via normally closed switches that are disposed in parallel to the blanking/protection components. When power is provided to the protection device (1300), a signal (1304) corresponding to the power can open the normally closed switches. In some embodiments, the protection device (1300) may include additional circuit protection and filtering functionality configured to reduce peak-to-peak voltages of high slew rate and/or high voltage signals, even when the protection device (1300) is un-powered and/or when the electrical component(s) (1310) are not isolated from the patient (1320). The protection device (1300) may include one or more of a passive filter device (1330) (as described above with reference to FIG. 2), common mode protection device (1340), and differential/high voltage protection device (1350), which may include one or more common and differential mode chokes using ferrites/magnetics, inductor and capacitor-based filters, and differential high voltage and differential clamping components including one or more of transient-voltage-suppression (TVS) diodes/tranzorbs, gas discharge tubes, and thyristors. In some embodiments, the methods, systems, and devices disclosed herein may comprise one or more of the methods, systems, and devices described in U.S. Application Ser. No. 62/667,887, filed on May 7, 2018, and titled "SYSTEMS, APPARATUSES, AND METHODS FOR FILTERING HIGH VOLTAGE NOISE INDUCED BY PULSED ELECTRIC FIELD ABLATION," incorporated above in its entirety.

Figure 16:
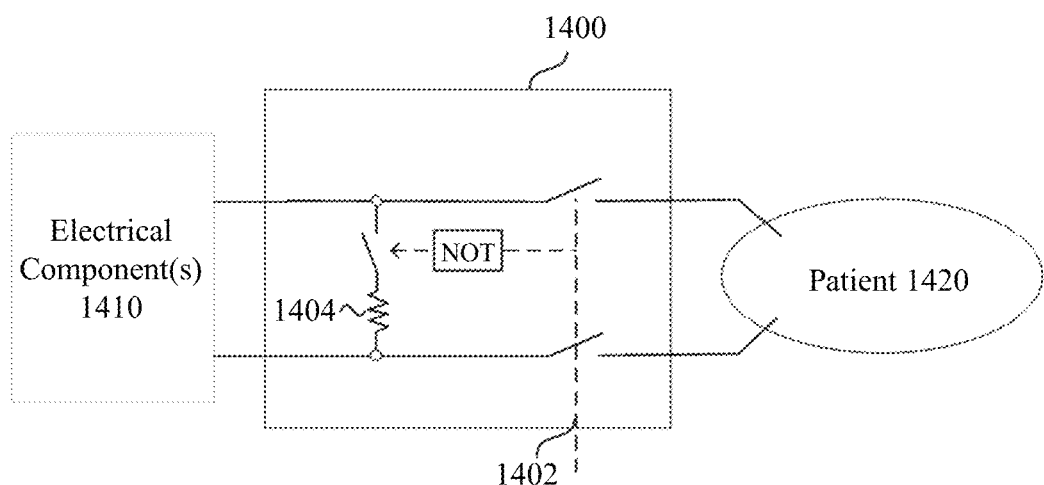
FIG. 16 is a schematic diagram of a protection device for controlling connections between electronic components operating in a high voltage exposure area, according to embodiments.

In some cardiac stimulators (e.g., electrophysiology laboratory stimulator systems), patient connections may be monitored for high impedance to alert a user of disconnections. To prevent undesirable warnings during use of a protection device (e.g., during blanking intervals), a fixed known impedance (e.g., by way of a fixed resistor having a value in a range expected by the stimulator such as, for example, 1 kOhm) can be provided to the connections to the stimulator. FIG. 16 is a block diagram of electrical component(s) (1410) coupled to a patient (1420). One or more electrical component(s) (1410) (e.g., cardiac stimulator) may be coupled to the patient (1420) via a protection device (1400) configured to selectively electrically isolate such components from devices disposed in the heart of the patient (1420) via a signal (1402). A cardiac stimulator included in the electrical component(s) (1410) may continuously monitor the electrical connection to the patient (1420) and generate a disconnection signal (e.g., alarm signal to the user) when disconnection (e.g., high-impedance) is detected. In some embodiments, in order to inhibit generation of a disconnection signal by the system (1410) during a protection interval of the protection device (1400), the protection device (1400) may provide the cardiac stimulator with a predetermined impedance (1440) (e.g., between about 100 Ohm and about 10 kOhms) in a range that the stimulator would expect to correspond to normal operations. For example, the protection device (1400) operating during the protection interval may send a signal to close a switch in series with a resistor (1440) that can then provide the fixed impedance value. The quick transition between "patient connection" and "open-circuit with fixed resistor load" can be sufficiently fast to prevent any warnings or alerts by the cardiac stimulator. In some embodiments it may be useful to switch-in the load to the electrical component first, a short time interval before disconnecting the patient connections (on the order of 1 us to 100 us). If this is done, there is not a small amount of time when the electrical component sees an open-circuit. The patient-connections should then be connected just before the resistive load is disconnected. Another implementation optimization is to provide the "load resistor" on both sides (patient side as well) so that there is symmetry in the implementation and the protection device may be plugged in either way.

Figure 17A:
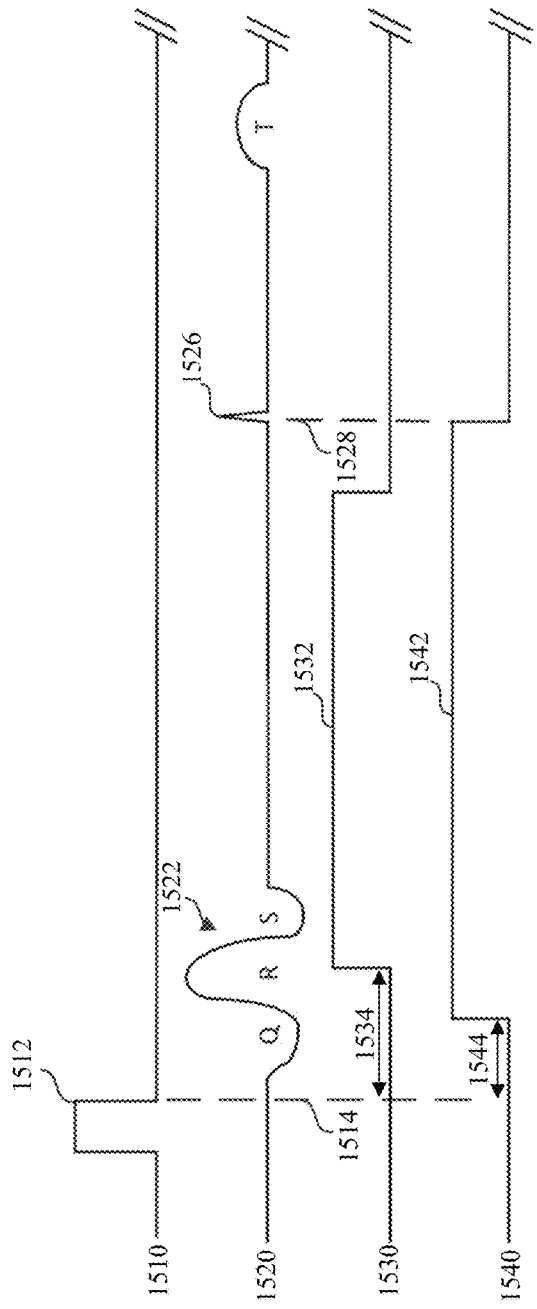
FIGS. 17A and 17B illustrate time sequences of a cardiac pacing signal, cardiac activity, energy delivery, and device isolation, according to embodiments.
Figure 17B:
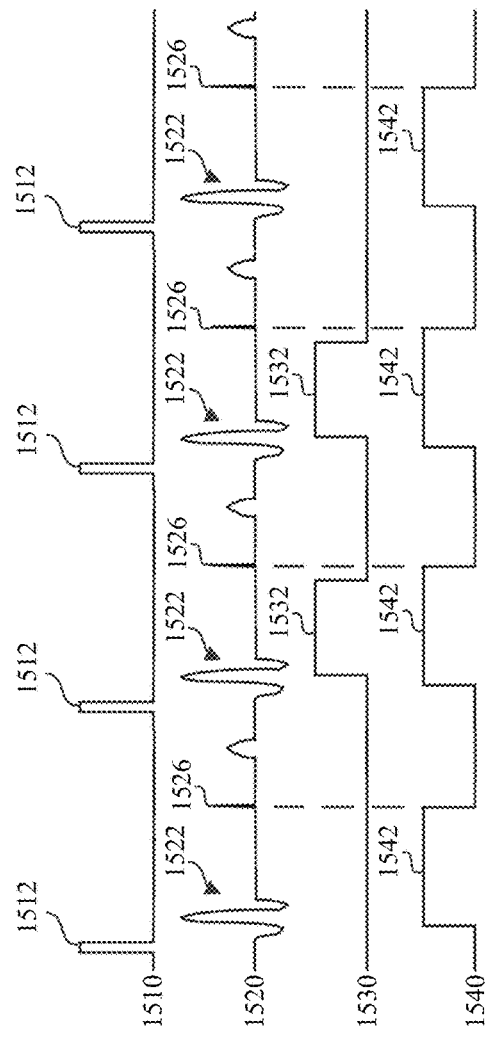

In some instances, with a protection device as implemented in FIG. 16, there may be introduction of switching artifacts and short voltage spikes on the patient. FIGS. 17A and 17B are schematic illustrations of a time sequence of cardiac stimulation (1510), electrocardiogram (1520), pulsed field ablation delivery (1530), and protection interval (1540) channels, where a switching artifact (1526) may occur when a protection interval ends. FIG. 17A illustrates a single cardiac cycle and FIG. 17B illustrates a plurality of cardiac cycles, as described in more detail herein. The stimulation or pacing signal (1510) may be periodic and may comprise a rectangular pulse having a width of between about 0.1 ms and about 100 ms. In some embodiments, the pacing pulses (1512) may be delivered using any of the pacing devices (e.g., pacing devices (230, 630, 1030)) described herein. The pacing pulses (1512) may correspond to one or more of ventricular and atrial cardiac pacing. In response to the pacing pulses (1512), the cardiac cycle of the heart may synchronize with the pacing pulses (1512). For example, the QRS waveform (1522) in FIGS. 17A and 17B is synchronized with the pacing pulse (1512).

In some embodiments, a pulse waveform (1532) and protection interval (1542) may synchronize with one or more of the pacing signal (1512) and the cardiac cycle (e.g., via R-wave detection), as described in embodiments above. For example, a pulse waveform (1532) may have a first length and a protection interval (1542) may have a second length at least as long as the first length. The pulse waveform (1532) may be delivered after a first delay (1534) from a trailing edge (1514) of the cardiac pacing pulse (1512). The first delay (1534) may be a predetermined value. For example, the first delay (1534) may be between about 1 ms and about 20 ms. Likewise, a protection interval (1542) may synchronize with the cardiac pacing pulse (1512) after a second delay (1544). In this manner, a cardiac pacing signal (1512) may be configured to trigger the pulse waveform (1532) and the protection interval (1542).

In embodiments including a protection device as implemented in FIG. 16, switching artifact (1526) (e.g., voltage spike) may be introduced in the patient and picked up in the electrocardiogram (1520) (e.g., via an electrocardiogram recording system) that may interfere with analysis of cardiac activity. For example, a protection artifact (1526) may coincide with a trailing edge (1528) of a protection interval (1542). FIG. 17B illustrates an embodiment where a protection interval (1542) is provided for each heartbeat and may, for example, generate an artifact (1526) for each protection interval/heartbeat. In some embodiments where less coordinated control of a protection device is available, one or more protection intervals (1542) may be provided without a corresponding pulse waveform (1532). This may occur, for example, in embodiments where the pulse waveform (1530) and protection signal (1540) are independently synchronized using different signals.

When artifacts (1526) are sufficiently large in magnitude, they can cause clinical misinterpretation of cardiac activity. To mitigate this risk, several options are available. First, the protection module can be integrated with a signal generator such that the protection interval (1542) is provided only when there is a corresponding pulse waveform (1532) and not when a pulse waveform (1532) is not delivered. Accordingly, a protection interval (1542) is provided when necessary to electrically isolate a cardiac stimulator or other protected electrical components from a high voltage pulse waveform. With this implementation, no unnecessary protection-switching occurs, and for artifacts (1526) generated with a pulse waveform, the high voltage ablation energy delivered to heart tissue saturates the heartbeats such that the artifacts (1526) do not present an issue.

Second, for independent protection devices where less coordinated control with pulsed field ablation device is possible, switching artifacts (1526) can be reduced, e.g., using placement of low-value capacitors across the isolation switches or between the protected channels to absorb some of the high-frequency local switching energy in the protection device. The implementation of previously described passive filtering components, e.g., see FIG. 2, can also be implemented to reduce artifacts (1526). Other options include using additional switches/MOSFETs to temporarily short pairs of signals together (e.g., stimulator +/− and patient +/−) before re-connecting to the patient, temporarily switching in a resistive load on the patient-side during a blanking interval, etc.

Figure 18:
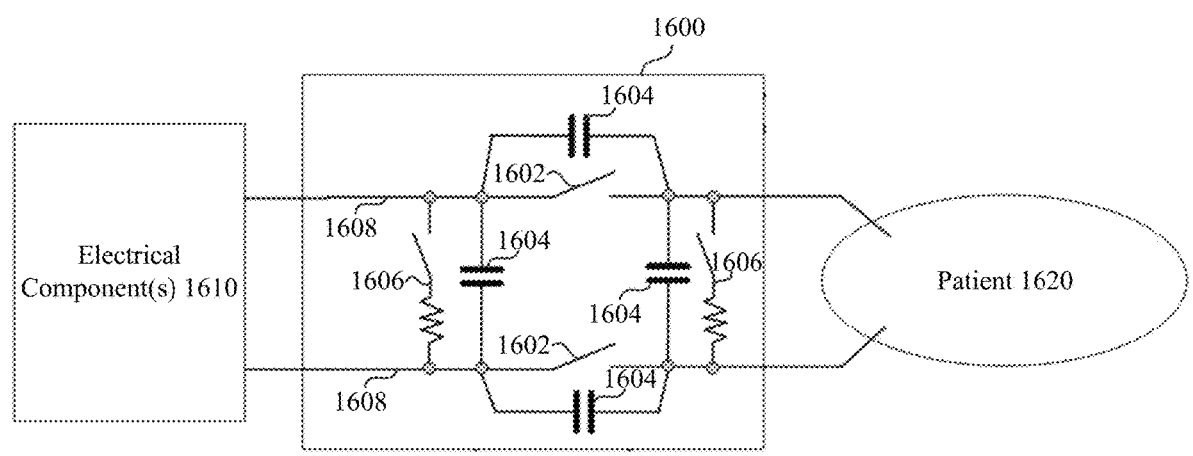
FIG. 18 is a schematic diagram of a protection device for controlling connections between electronic components operating in a high voltage exposure area, according to embodiments.

FIG. 18 is a block diagram of electrical component(s) (1610) coupled to a patient (1620) via a protection device (1600) including one or more capacitors for reducing artifacts. One or more electrical component(s) (1610) (e.g., cardiac stimulator) may be coupled to the patient (1620) via a protection device (1600) configured to selectively electrically isolate such components from devices disposed in the heart of the patient (1620). In some embodiments, the protection device (1600) may be configured to reduce a magnitude of an artifact (e.g., artifact (1526)).

The protection device (1600) may include one or more series protection switches (1602) and resistors (1606). The protection device (1600) may further include one or more of capacitors (1604) configured parallel to corresponding switches (1602) and resistors (1606). The capacitors (1604) may be configured to receive a portion of any voltage spike generated by the switching operations of protection device (1600). Additionally or alternatively, the protection device (1600) may include one or more circuit components described in FIG. 15 (e.g., filter device (1330), common mode protection device (1340), differential/high voltage protection device (1350)) configured to reduce switching artifacts.

The resistors (1606) can be arranged in series with switches that can be configured to close prior to closing the series protection switches (1602) to reduce artifacts produced by the switching of the protection switches (1602). For example, the switches in series with the resistors (1606) may be configured to close prior to the series protection switches (1602) closing in order to provide a temporary pathways for one or more of the electrical component(s) (1610) and the patient (1620), thereby reducing risk of artifacts from the series protection switches (1602) when the loads are subsequently disconnected.

It should be understood that the examples and illustrations in this disclosure serve exemplary purposes and departures and variations such number of electrodes and devices, and so on can be built and deployed according to the teachings herein without departing from the scope of this invention. In particular, whether ablation energy with high voltage pulse waveforms is delivered synchronously with cardiac pacing or asynchronously (e.g., without cardiac pacing), the systems, devices, and methods disclosed herein can be configured to protect a wide variety of medical electronic equipment including but not limited to cardiac stimulators, electroanatomical mapping systems, ECG recording systems, ECG monitoring systems, device navigation or tracking systems, etc. It should be appreciated that the protection device embodiments described herein can be implemented in multi-channel formats that can protect multiple device electrodes or sets of device electrodes that may be connected to such electronic equipment. For example, the protection device can incorporate 2, 4, 6, 8, 64, 256, or 512 channels of protection. Furthermore, the control signal used for activation of the protection device(s) can be output to multiple such devices, thus providing an expandable protection device where the number of channels of protection can be expanded in modular fashion.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

Some embodiments described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which may include, for example, the instructions and/or computer code disclosed herein.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware)

may be expressed in a variety of software languages (e.g., computer code), including C, C++, Java®, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

The specific examples and descriptions herein are exemplary in nature and embodiments may be developed by those skilled in the art based on the material taught herein without departing from the scope of the present invention.

We claim:

1. A system, comprising:
a set of electrodes disposable near cardiac tissue of a heart;
a set of sensors disposable near patient anatomy;
a signal generator configured to generate a pulse waveform, the signal generator coupled to the set of electrodes and configured to repeatedly deliver the pulse waveform to the set of electrodes, the set of electrodes configured to generate a pulsed electric field in response to the delivery of the pulse waveform to ablate the cardiac tissue;
a protection circuit configured to selectively couple and decouple an electronic device to the set of the sensors; and
a processor coupled to the protection circuit and configured to control the protection circuit to transition between a closed-circuit configuration and an open-circuit configuration, the protection circuit in the closed-circuit configuration configured to couple the electronic device to the set of sensors to enable signals to be sent between the set of sensors and the electronic device, the protection circuit in the open-circuit configuration configured to decouple the electronic device from the set of sensors such that the electronic device is electrically isolated from the set of sensors, the processor configured to control the protection circuit to transition into the open-circuit configuration during intervals of time beginning before and ending after each delivery of the pulse waveform to the set of electrodes such that the electronic device is isolated from voltages and currents induced in response to the delivery of the pulse waveform to the set of electrodes,
the protection circuit including at least one switch component configured to switch between a conducting state in which the electronic device is coupled to the set of sensors and a non-conducting state in which the electronic device is decoupled from the set of sensors, the at least one switch component including a pair of metal oxide semiconductor field effect transistors (MOSFETs),
the pair of MOSFETs having a common source terminal and gate terminals coupled to one or more isolated gate drive circuits, the one or more isolated gate drive circuits configured to deliver a control signal to the gate terminals to switch the pair of MOSFETs between the conducting state and the non-conducting state.

2. The system of claim 1, wherein the electronic device includes at least one of:
an electroanatomical mapping system configured to generate a map of cardiac electrical activity;
a device tracking and navigation system configured to generate an anatomical map of a cardiac chamber; or
an electrocardiogram (ECG) system configured to monitor cardiac electrical activity.

3. The system of claim 1, further comprising a signal detector configured to detect an R-wave associated with each cardiac cycle from a set of cardiac cycles,
the signal generator configured to deliver the pulse waveform during each cardiac cycle from the set of cardiac cycles after detection of the R-wave of that cardiac cycle.

4. The system of claim 3, wherein the signal generator is configured to deliver the pulse waveform spaced from the R-wave of each cardiac cycle from the set of cardiac cycles by a time delay, the time delay enabling the electronic device to be decoupled from the set of sensors before delivery of the pulse waveform.

5. The system of claim 3, wherein the processor is further configured to:
receive trigger signals from the signal detector, each trigger signal indicating when the R-wave has been detected,
the processor configured to control the protection circuit to transition into the open-circuit configuration in response to receiving each trigger signal; and
the processor configured to control the protection circuit to transition into the closed-circuit configuration after each delivery of the pulse waveform.

6. The system of claim 1, wherein the protection circuit is integrated into the signal generator.

7. The system of claim 6, wherein the processor is further configured to coordinate the delivery of the pulse waveform to the set of electrodes with the transitioning of the protection circuit into the open-circuit configuration.

8. The system of claim 1, wherein the at least one switch component is a first switch component, the protection circuit further including a second switch component configured to be in a conducting state when the protection circuit is powered off and a non-conducting state when the protection circuit is powered on, the second switch component being arranged in parallel with the first switch component such that the electronic device is coupled to the set of sensors when the protection circuit is powered off.

9. The system of claim 1, wherein the protection circuit further includes one or more of: a common mode choke, a differential mode choke, or a filter circuit.

10. The system of claim 1, wherein the protection circuit further includes at least (i) one or more capacitors, or (ii) switched-in resistors configured to absorb energy associated with the at least one switch component switching between the conducting state and the non-conducting state.

11. The system of claim 1, wherein the protection circuit is configured to selectively couple and decouple a plurality of electronic devices from a plurality of sets of sensors, the plurality of electronic devices including the electronic device and the plurality of sets of sensors including the set of sensors.

12. The system of claim 1, wherein the protection circuit is coupled between the electronic device and the set of sensors.

13. The system of claim 1, wherein the electronic device is a cardiac stimulation device configured to deliver pacing signals to the heart.

14. The system of claim 1, wherein at least one of the set of sensors is an electrode.

15. The system of claim 1, wherein at least one of the set of sensors is an electromagnetic tracking sensor.

16. The system of claim 1, wherein the at least one switch component includes a relay switch.

17. An apparatus, comprising:
a set of electrodes disposable near cardiac tissue of a heart;
a signal generator coupled to the set of electrodes and configured to generate a pulse waveform;
a set of sensors disposable near patient anatomy;
at least one switch component coupled between an electronic device and the set of sensors, the at least one switch component configured to switch between a conducting state in which the electronic device is coupled to the set of sensors and a non-conducting state in which the electronic device is decoupled from the set of sensors, the at least one switch component including a pair of metal oxide semiconductor field effect transistors (MOSFETs), the pair of MOSFETs having a common source terminal and gate terminals coupled to one or more isolated gate drive circuits, the one or more isolated gate drive circuits configured to deliver a control signal to the gate terminals to switch the pair of MOSFETs between the conducting state and the non-conducting state; and
a processor coupled to the signal generator and the at least one switch component, the processor configured to:
receive trigger signals from the signal generator; and
in response to receiving each trigger signal:
set the at least one switch component to the non-conducting state such that the electronic device is decoupled from the set of sensors; and
deliver, via the signal generator and after setting the at least one switch component to the non-conducting state, the pulse waveform to the set of electrodes such that the set of electrodes generates a pulsed electric field; and
set, after delivering the pulse waveform, the at least one switch component to the conducting state such that the electronic device is coupled to the set of sensors and can send signals to or receive signals from the set of sensors.

18. The apparatus of claim 17, wherein the processor is configured to receive the trigger signals from a cardiac stimulation device configured to generate pacing signals, each trigger signal indicating delivery of a pacing signal to the heart.

19. The apparatus of claim 17, wherein the processor is configured to receive the trigger signals from a signal detector configured to detect an R-wave associated with a cardiac cycle of the heart, each trigger signal indicating the R-wave being detected by the signal detector.

20. The apparatus of claim 17, wherein the at least one switch component is a first switch component, the apparatus further comprising a second switch component configured to be in a conducting state when power is not being delivered to the first switch component and a non-conducting state when the power is being delivered to the first switch component, the second switch component being arranged in parallel with the first switch component such that the electronic device is coupled to the set of sensors when the power is not being delivered to the first switch component.

21. The apparatus of claim 17, wherein the at least one switch component in the non-conducting state isolates the electronic device from the set of sensors to protect the electronic device from voltages and currents induced at the set of sensors in response to delivering the pulse waveform to the set of electrodes.

22. The apparatus of claim 17, wherein the at least one switch component includes a relay switch.

23. An apparatus, comprising:
a set of electrodes disposable near cardiac tissue of a heart;
a signal generator coupled to the set of electrodes and configured to generate a pulse waveform;
a set of sensors disposable near patient anatomy;
at least one switch component coupled between an electronic device and the set of sensors, the at least one switch component configured to switch between a conducting state in which the electronic device is coupled to the set of sensors and a non-conducting state in which the electronic device is decoupled from the set of sensors, the at least one switch component including a pair of metal oxide semiconductor field effect transistors (MOSFETs), the pair of MOSFETs having a common source terminal and gate terminals coupled to one or more isolated gate drive circuits, the one or more isolated gate drive circuits configured to deliver a control signal to the gate terminals to switch the pair of MOSFETs between the conducting state and the non-conducting state; and
a processor coupled to the signal generator and the at least one switch component, the processor configured to:
determine to deliver the pulse waveform to the set of electrodes during a set of cardiac cycles; and
for each cardiac cycle from the set of cardiac cycles:
set the at least one switch component to the non-conducting state such that the electronic device is decoupled from the set of sensors; and
deliver, via the signal generator and after setting the at least one switch component to the non-conducting state, the pulse waveform to the set of electrodes such that the set of electrodes generates a pulsed electric field; and
set, after delivering the pulse waveform, the at least one switch component to the conducting state such that the electronic device is coupled to the set of sensors and can send signals to or receive signals from the set of sensors.

24. The apparatus of claim 23, wherein the at least one switch component is a first switch component, the apparatus further comprising a second switch component configured to be in a conducting state when power is not being delivered to the first switch component and a non-conducting state when the power is being delivered to the first switch component, the second switch component being arranged in parallel with the first switch component such that the electronic device is coupled to the set of sensors when the power is not being delivered to the first switch component.

25. The apparatus of claim 23, wherein the at least one switch component in the non-conducting state isolates the electronic device from the set of sensors to protect the electronic device from voltages and currents induced at the set of sensors in response to delivering the pulse waveform to the set of electrodes.

* * * * *